United States Patent
Zhao et al.

(10) Patent No.: US 9,637,443 B2
(45) Date of Patent: May 2, 2017

(54) GRAPHENE QUANTUM DOTS AND METHOD OF MAKING

(71) Applicant: University of North Dakota, Grand Forks, ND (US)

(72) Inventors: Julia Xiaojun Zhao, Grand Forks, ND (US); Xu Wu, Grand Forks, ND (US)

(73) Assignee: University of North Dakota, Grand Forks, ND (US)

( * ) Notice: Subject to any disclaimer, the term of this patent is extended or adjusted under 35 U.S.C. 154(b) by 153 days.

(21) Appl. No.: 14/261,936

(22) Filed: Apr. 25, 2014

(65) Prior Publication Data

US 2015/0284318 A1  Oct. 8, 2015

Related U.S. Application Data

(60) Provisional application No. 61/815,866, filed on Apr. 25, 2013.

(51) Int. Cl.
| | |
|---|---|
| *A61K 9/00* | (2006.01) |
| *C07C 235/00* | (2006.01) |
| *H01L 29/12* | (2006.01) |
| *H01L 29/16* | (2006.01) |
| *H01L 51/00* | (2006.01) |
| *A61K 49/00* | (2006.01) |
| *B01J 31/04* | (2006.01) |

(Continued)

(52) U.S. Cl.
CPC ........ *C07C 235/00* (2013.01); *A61K 49/0017* (2013.01); *B01J 31/04* (2013.01); *C01B 31/0438* (2013.01); *C07C 231/00* (2013.01); *G01N 33/5005* (2013.01); *G01N 33/588* (2013.01); *H01L 29/127* (2013.01); *H01L 29/1606* (2013.01); *H01L 51/0045* (2013.01); *B01J 2231/62* (2013.01); *B82Y 30/00* (2013.01); *B82Y 40/00* (2013.01); *H01L 51/502* (2013.01)

(58) Field of Classification Search
CPC .................................................. C07C 235/00
See application file for complete search history.

(56) References Cited

U.S. PATENT DOCUMENTS

2008/0255294 A1  10/2008  Yerushalmi-Rozen

FOREIGN PATENT DOCUMENTS

| | | | |
|---|---|---|---|
| CN | 102190296 A | * | 9/2011 |
| CN | 102849722 A | * | 1/2013 |
| WO | 2012016296 A1 | | 2/2012 |

OTHER PUBLICATIONS

Machine translation of CN 10219296A, 2016.*

(Continued)

*Primary Examiner* — Paul Dickinson
(74) *Attorney, Agent, or Firm* — Kinney & Lange, P.A.

(57) ABSTRACT

A method for forming a graphene quantum dot product includes adding an organic starting material to a vessel and heating the organic starting material to a temperature within 20° C. of the organic starting material's boiling temperature for a time no longer than ten minutes to form graphene quantum dots. A method for sensing a graphene quantum dot includes forming a graphene quantum dot, exciting the graphene quantum dot with light having a first wavelength, measuring light emitted by the excited graphene quantum dot at a second wavelength different from the first wavelength. A graphene quantum dot includes carbon atoms and nitrogen atoms where the nitrogen atoms are present within the graphene quantum dot at a level between 6.0% and 11.0% of a level of carbon atoms present in the graphene quantum dot.

12 Claims, 23 Drawing Sheets

(51) Int. Cl.
C07C 231/00 (2006.01)
G01N 33/50 (2006.01)
G01N 33/58 (2006.01)
C01B 31/04 (2006.01)
B82Y 40/00 (2011.01)
H01L 51/50 (2006.01)
B82Y 30/00 (2011.01)

(56) References Cited

OTHER PUBLICATIONS

Li et al, Synthesis and upconversion luminescence of N-doped graphene quantum dots, Appl. Phys. Lett., 2012, 101, 103-107.*
Machien translation of CN 102849722, 2016.*
Wang et al, Nitrogen-Doped Graphene and its Application in Electrochemical Biosensing, ACS Nano, 2010, 4(4), 1790-1798.*
Li et al., Synthesis and upconversion luminescence of N-doped graphene quantum dots, Applied Physics Letters, Aug. 18, 2014, 2 pages.
Tang et al., Deep Ultraviolet Photoluminescence of Water-Soluble Self-Passivated Graphene Quantum Dots, ACS Nano, Aug. 18, 2014, 9 pages.
Wang et al., Nitrogen-Doped Graphene and Its Application in Electrochemical Biosensing, ACS Nano, Aug. 18, 2014, 3 pages.
Peng et al., Graphene Quantum Dots Derived from Carbon Fibers, Nano Letters, Aug. 18, 2014, 6 pages.
Li et al., Nitrogen-Doped Graphene Quantum Dots with Oxygen-Rich Functional Groups, Journal of the American Chemical Society, Aug. 18, 2014, 4 pages.
Sinha et al., Preparation of silver powder through glycerol process, Bulletin of Material Science, Aug. 18, 2014, 5 pages.
International Searching Authority, PCT Notification of Transmittal of the International Search Report and the Written Opinion, Sep. 8, 2014, 11 pages.

* cited by examiner

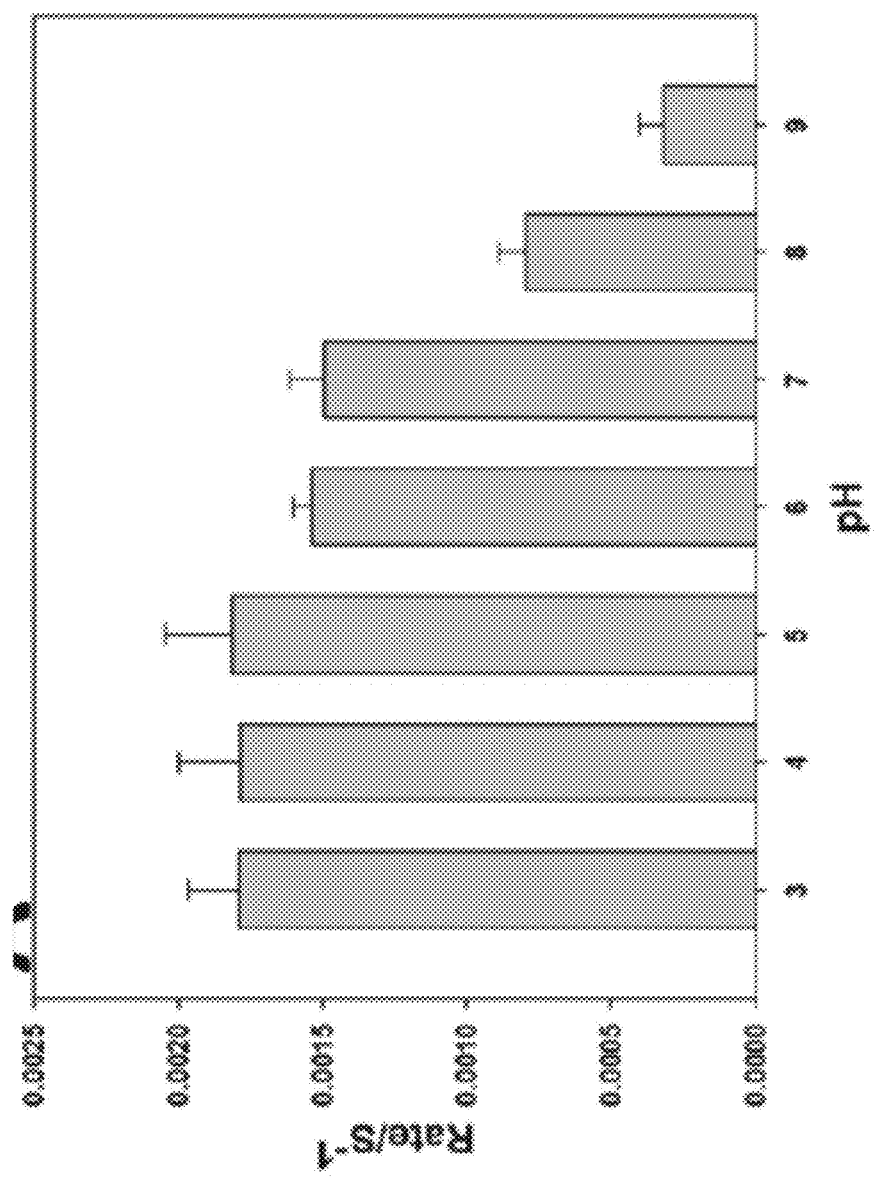

US 9,637,443 B2

GRAPHENE QUANTUM DOTS AND METHOD OF MAKING

CROSS REFERENCE TO RELATED APPLICATION

This patent application claims priority to U.S. application Ser. No. 61/815,866, filed on Apr. 25, 2013 and entitled "GRAPHENE QUANTUM DOTS DERIVED FROM GLUTAMIC ACID", which is hereby incorporated by reference in its entirety.

STATEMENT OF GOVERNMENT INTEREST

This invention was made with government support under Grant No. CHE0947043 awarded by the National Science Foundation. The government has certain rights in the invention.

BACKGROUND

Graphene quantum dots (GQDs) are single atom thick sheets of graphene that generally have no dimension greater than 100 nanometers (nm). GQDs can be used in a wide variety of applications ranging from electronics, optoelectronics and electromagnetics. The electrical, magnetic, optical and chemical properties of GQDs are governed by their size and edge crystallography. Compared to graphene, GQDs exhibit stronger photoluminescence useful in bioimaging, biosensing and light-emitting diodes.

A number of methods have been developed to synthesize GQDs. These methods generally fall into two groups: "top-down" and "bottom-up" methods. In top-down methods, larger carbon materials such as carbon nanotubes, graphene sheets and carbon fibers are cut to form the smaller GQDs. In bottom-up methods, GQDs are fabricated from smaller carbon precursors. Glucose, hexa-peri-hexabenzocoronene and citric acid have been used to form GQDs using bottom-up methods. However, bottom-up methods in current use require harsh, time consuming and/or complicated conditions, which include the use of strong acids and alkali, long treatment times and separation processes.

SUMMARY

A method for forming a graphene quantum dot includes adding an organic starting material to a vessel and heating the organic starting material to a temperature within 20° C. of the organic starting material's boiling point for a time no longer than ten minutes to form graphene quantum dots. The organic starting material is a hydrophilic compound that has at least two functional groups selected from carboxyl groups and hydroxyl groups.

A method for sensing a graphene quantum dot includes heating an organic starting material to a temperature within 20° C. of the organic starting material's boiling point for a time no longer than ten minutes to form a graphene quantum dot, exciting the graphene quantum dot with light having a first wavelength, and measuring light emitted by the excited graphene quantum dot at a second wavelength different from the first wavelength. The organic starting material is a hydrophilic compound that has at least two functional groups selected from carboxyl groups and hydroxyl groups.

A graphene quantum dot includes carbon atoms and nitrogen atoms where the nitrogen atoms are present within the graphene quantum dot at a level between 6.0% and 11.0% of a level of carbon atoms present in the graphene quantum dot.

A method for forming a graphene quantum dot includes adding an organic starting material to a vessel and heating the organic starting material for a time no longer than ten minutes to pyrolyze the organic starting material and from graphene quantum dots. The organic starting material is a hydrophilic compound that has at least two functional groups selected from carboxyl groups and hydroxyl groups.

BRIEF DESCRIPTION OF THE DRAWINGS

FIGS. 15A, 15B, 15C and 15D are graphs illustrating the effect of pH, temperature, ABTS concentration and GQD concentration, respectively, on the peroxidase-like catalytic activity of GQDs.

DETAILED DESCRIPTION

According to embodiments of the present disclosure, graphene quantum dots (GQDs) are prepared according to a bottom-up method by pyrolyzing an organic starting material to form GQDs. Key factors in determining the GQD precursors (organic starting materials) and formation method was the desire to use non-toxic and natural precursors and common reaction materials. The methods for making GQDs described herein do not require the use of hazardous reagents and chemicals like some other methods. In one particular embodiment, glutamic acid is used to form Glu-GQDs. Glutamic acid contains amine groups that can be easily modified and do not require further capping.

GQDs are formed by adding an organic starting material to a vessel and heating the organic starting material to a temperature that is within 20° C. of the organic starting material's boiling temperature. The heating takes place for a time no longer than ten minutes. During this heating step, the organic starting material is pyrolyzed, forming GQDs.

One example of a suitable organic starting material is glutamic acid. Methods for forming GQDs (Glu-GQDs) will be described with particular reference to glutamic acid. Glutamic acid is an amino acid having the molecular formula $C_5H_9NO_4$ and the following structure:

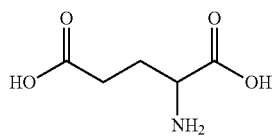

Figure 1:
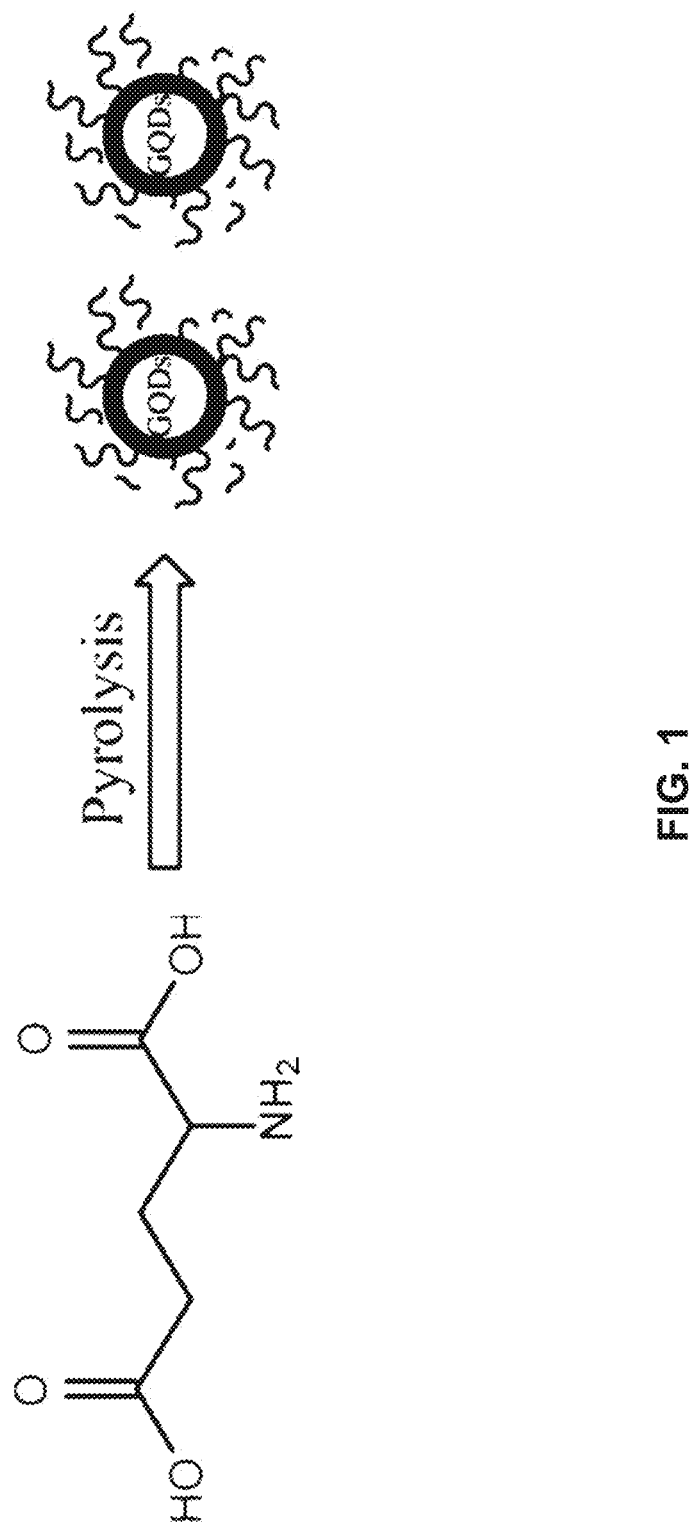
FIG. 1 is a schematic diagram showing the formation of GQDs through pyrolysis of glutamic acid.

To form Glu-GQDs, glutamic acid is added to a vessel and heated to a temperature within 20° C. of its boiling temperature to pyrolyze the glutamic acid. FIG. 1 illustrates a schematic diagram of the formation of Glu-GQDs through pyrolysis of glutamic acid. Glutamic acid has a boiling temperature of about 205° C. Thus, the glutamic acid is heated to a temperature between about 185° C. and about 225° C. according to the present disclosure. In some embodiments, the glutamic acid is heated to 210° C. (just above the boiling temperature of glutamic acid). The glutamic acid can be heated in an open vessel or a closed vessel.

The glutamic acid need only be heated to a temperature within 20° C. of its boiling point for a short period of time. Glutamic acid is exposed to the described temperature for less than ten minutes. Depending on the temperature selected, the time spent at that temperature may vary. In some embodiments, the glutamic acid is held at an elevated temperature for less than five minutes. In still other embodiments, the glutamic acid is held at an elevated temperature for less than 60 seconds. Higher temperatures generally require shorter periods of time. Thus, glutamic acid can be held at a temperature of about 185° C. for about ten minutes in one embodiment or held at a temperature of about 210° C. for about 45 seconds in another. In one particular embodiment, the glutamic acid is heated to 210° C. and is maintained at that temperature for about 45 seconds or less. In some embodiments, the glutamic acid is heated until it changes color. Glutamic acid is a solid at room temperature and has a melting temperature of 199° C. Unpyrolyzed glutamic acid, once melted, is generally a clear and colorless liquid. When heated above 200° C. for a short period of time (generally less than about 60 seconds), the glutamic acid becomes a pale yellow to brown liquid, indicating carbonization of glutamic acid as the result of pyrolysis. If the glutamic acid is heated to an elevated temperature for too long, the glutamic acid will turn black and Glu-GQDs will not be obtained.

After the glutamic acid has been heated for an appropriate length of time, a solvent can be added to the vessel containing the Glu-GQDs and the subsequently formed colloidal solution can be stirred. Adding a solvent helps to disperse the Glu-GQDs produced when the glutamic acid was heated. This helps to prevent the agglomeration and aggregation of Glu-GQDs within the heating vessel. In some embodiments, the solution is stirred for between about 15 minutes and about 60 minutes. In one particular embodiment, the solution is stirred for about about 30 minutes. In some embodiments, the solvent used is water, alcohols, such as ethanol, or a combination of water and an alcohol. Unlike other methods for forming GQDs, surface passivation agents or inorganic additives are not needed to produce Glu-GQDs according to the present disclosure.

After stirring, the colloidal solution is centrifuged. In some embodiments, the solution is centrifuged with a relative centrifugal force of about 10,000 g for between about 15 minutes and about 60 minutes. Following centrifugation, the supernatant is collected. The supernatant contains a concentrated Glu-GQD product (i.e. the supernatant has a higher concentration of Glu-GQDs than the overall colloidal solution). The Glu-GQDs present in the concentrated Glu-GQD product generally have an average diameter between 1 nanometer (nm) and 7 nm. In some embodiments, the Glu-GQDs contain between 55% and 65% carbon atoms, between 30% and 40% oxygen atoms, and between 3.5% and 7.5% nitrogen atoms. Unlike some other bottom-up formed GQDs, Glu-GQDs according to the present disclosure contain nitrogen atoms (from the glutamic acid amine group). In some embodiments, Glu-GQDs contain nitrogen atoms at a level between 6.0% and 11.0% of the level of carbon atoms present in the Glu-GQDs. Amine groups present in Glu-GQDs can provide active groups for surface modification of the Glu-GQDs.

The particular composition of Glu-GQDs formed according to the present disclosure allows their use in imaging and sensing applications and demonstrate improvements over GQDs produced by other bottom-up methods. For example, the fluorescence quantum yield of Glu-GQDs produced from glutamic acid is about five times higher than the yield of GQDs produced from citric acid. Glu-GQDs produced according to the present disclosure can be used for in vitro and in vivo fluorescence imaging. Glu-GQDs produced according to the present disclosure have also shown peroxidase-like catalytic activity and can be used to detect hydrogen peroxide ($H_2O_2$). Thus, Glu-GQDs are capable of catalyzing the reduction of $H_2O_2$.

While the formation of Glu-GQDs using glutamic acid has been described above, other organic starting materials can be used to form other GQDs. GQDs have also been successfully formed according to the methods described herein using tyrosine, maltose, glucose, sucrose, galactose, lactose and fructose. Based on these successes, it is expected that hydrophilic compounds having two or more carboxyl or hydroxyl functional groups will form GQDs according to the present disclosure. These hydrophilic compounds include those with any permutation of the two functional groups (i.e. two or more carboxyl groups, two or more hydroxyl groups, and one or more carboxyl groups with one or more hydroxyl groups). Thus, suitable organic starting materials are expected to include sugars and amino acids that have two or more carboxyl or hydroxyl functional groups. Combinations of different compounds that have similar boiling temperatures are also expected to be suitable. Therefore, in some embodiments, suitable organic starting materials include, but are not limited to, glutamic acid, aspartic acid, tyrosine, serine, threonine, maltose, glucose, sucrose, galactose, lactose, fructose and combinations thereof. The same parameters regarding heat (a temperature within 20° C. of the starting material's boiling point) and time (no longer than ten minutes) described above with respect to glutamic acid also apply to these other starting materials. Some other starting materials can also be heated until they turn from a generally colorless liquid to a darker shade (e.g., yellow, brown).

Figure 2:
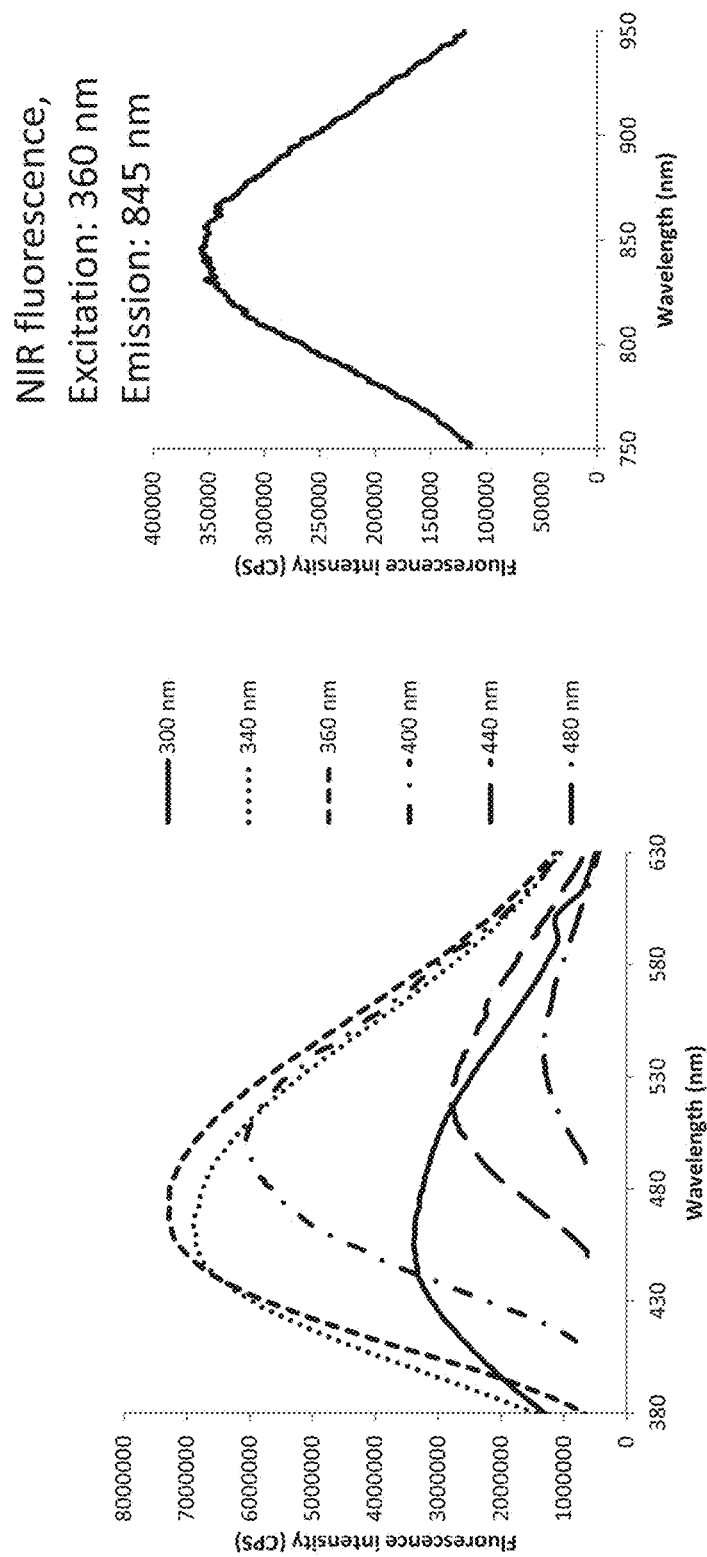
FIG. 2 illustrates fluorescence emission spectra of GQDs produced from maltose.
Figure 3:
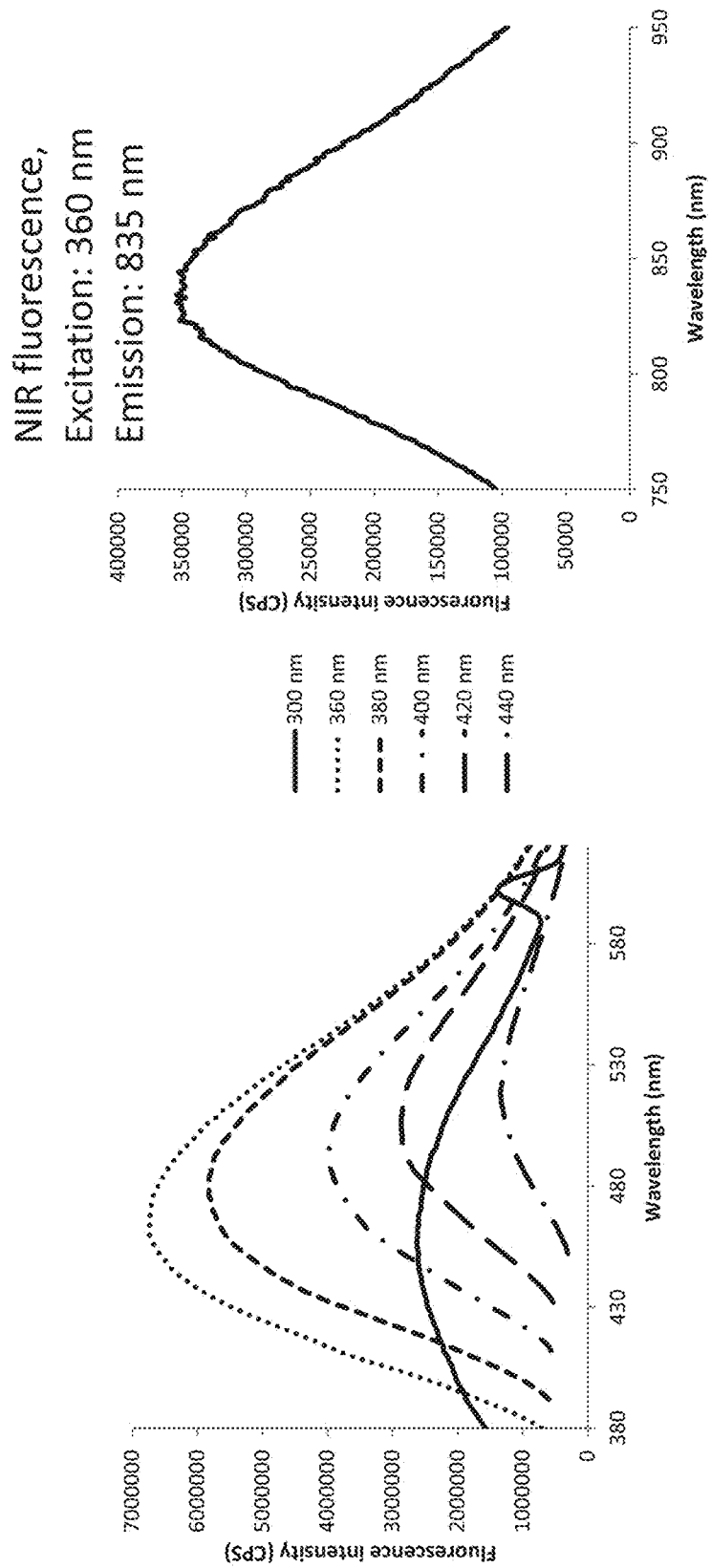
FIG. 3 illustrates fluorescence emission spectra of GQDs produced from glucose.
Figure 4:
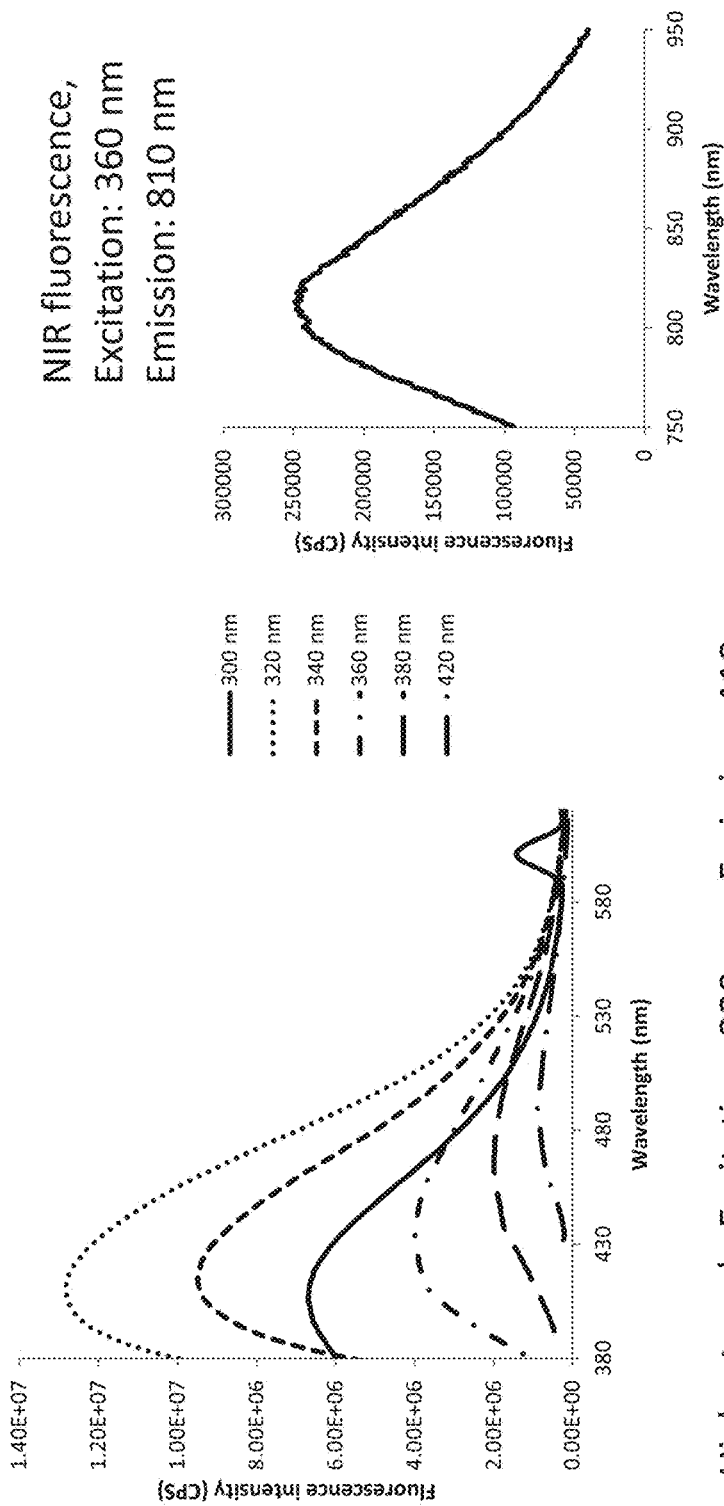
FIG. 4 illustrates fluorescence emission spectra of GQDs produced from tyrosine.
Figure 5:
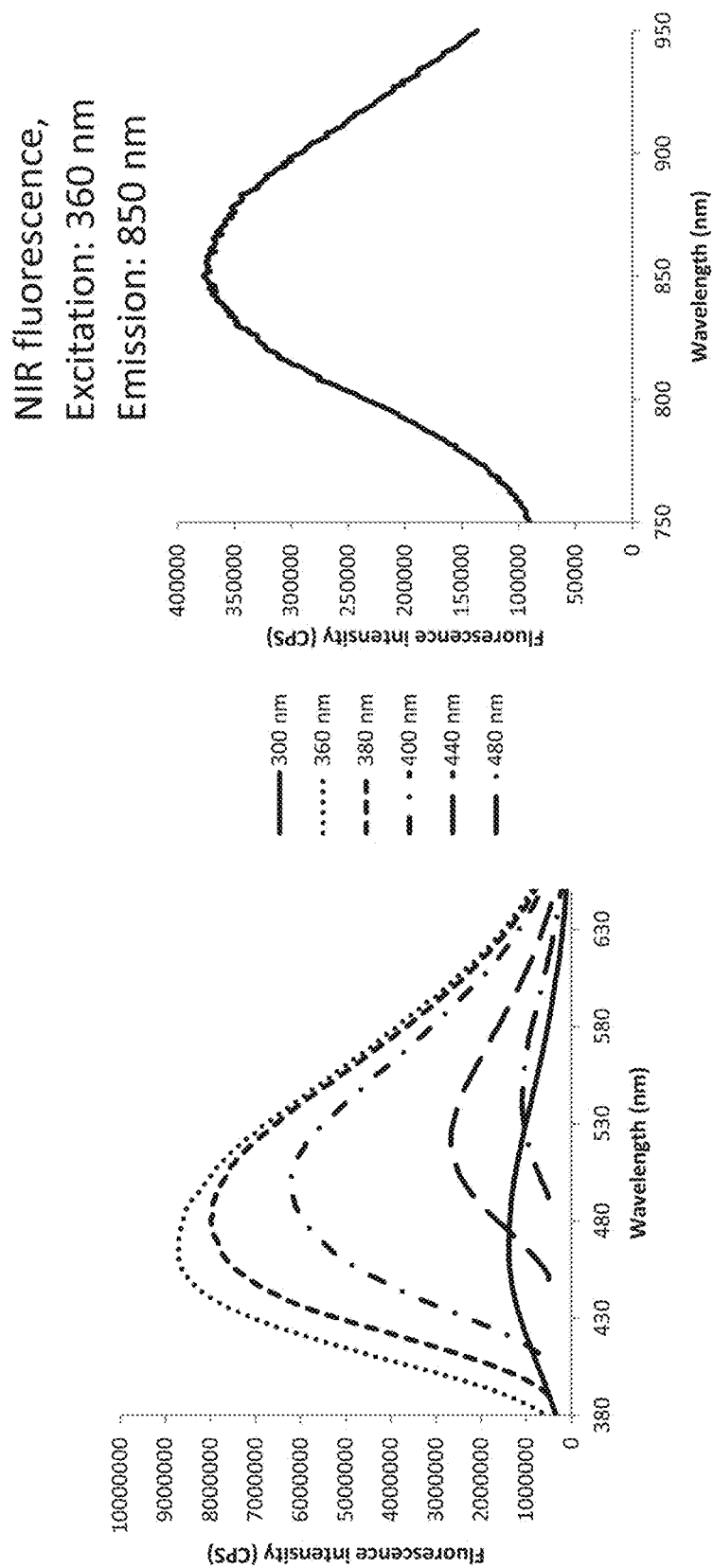
FIG. 5 illustrates fluorescence emission spectra of GQDs produced from sucrose.
Figure 6:
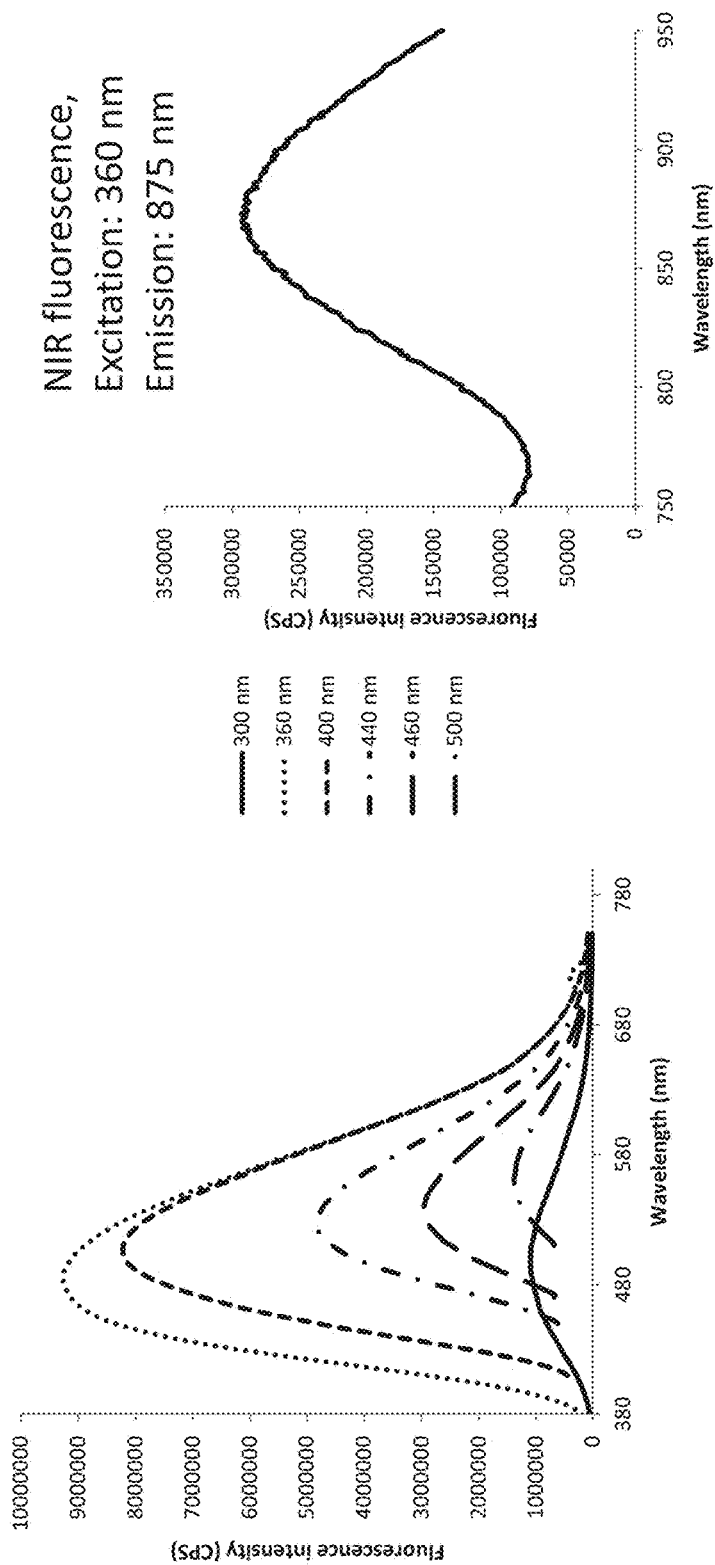
FIG. 6 illustrates fluorescence emission spectra of GQDs produced from galactose.
Figure 7:
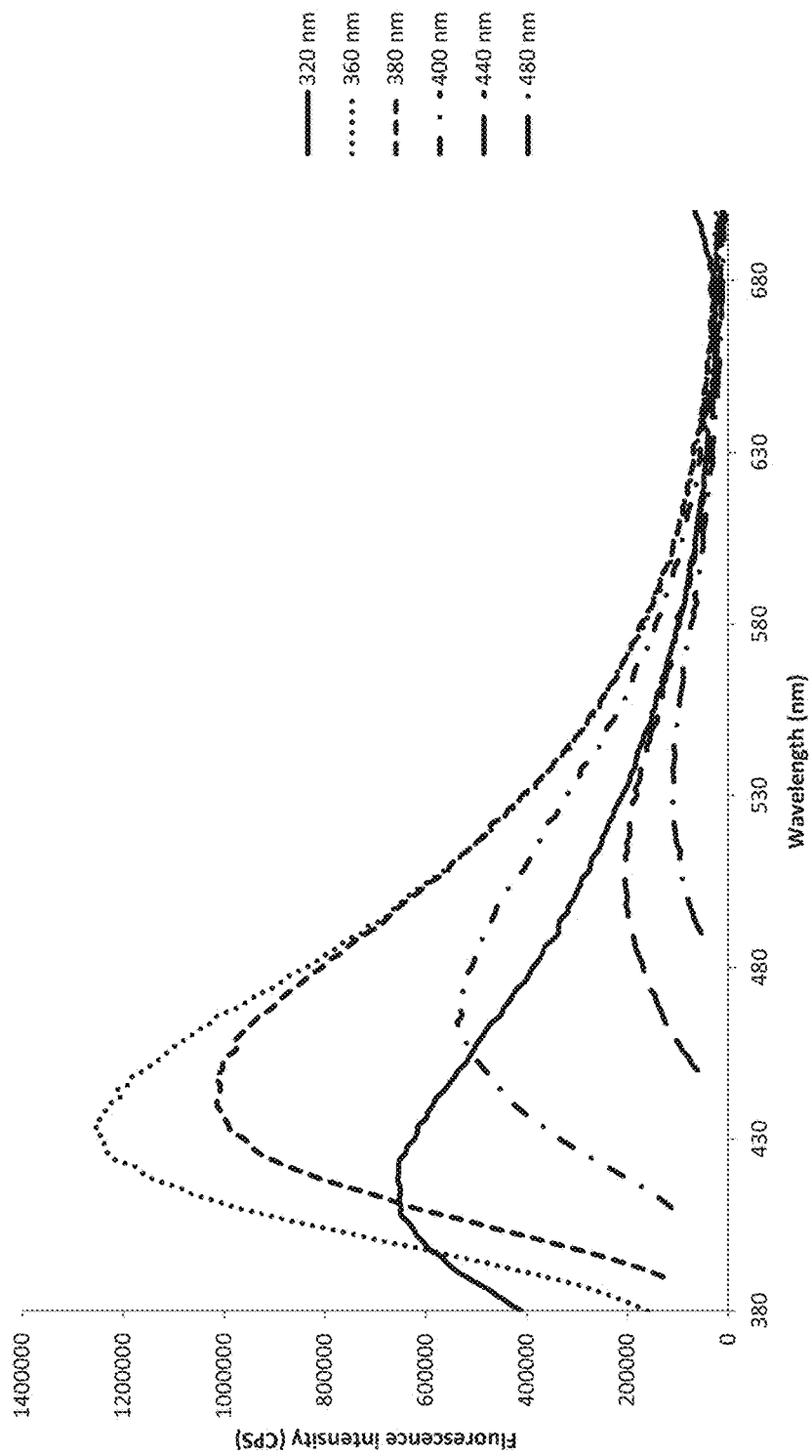
FIG. 7 illustrates fluorescence emission spectra of GQDs produced from glutamic acid according to FIG. 1.

The GQDs produced according to the present disclosure can be used for sensing applications as the GQDs exhibit fluorescence. One interesting property of the GQDs produced according to the methods described herein is that the emission wavelengths of the GQDs can be tuned based on the excitation wavelength. GQDs formed according to the present disclosure have peak emissions over a range of wavelengths depending on the starting material used to produce the GQDs and the excitation wavelength to which the GQDs are exposed. Generally, excitation wavelengths between 310 nm and 380 nm are used to excite the GQDs. Once excited at these wavelengths, the GQDs emit light having peak maximum wavelengths between 400 nm and 495 nm. The GQDs also emit light in the NIR range having relative maximum wavelengths between 800 nm and 885 nm. As shown in FIGS. 2-7, the tunable nature of the maximum intensity wavelength is demonstrated. FIGS. 2-6 also show the peak NIR emissions for GQDs. FIGS. 2-7, illustrate the fluorescence intensity of the emission wavelengths of maltose, glucose, tyrosine, sucrose, galactose and glutamic acid, respectively, based on a number of different excitation wavelengths. For example, FIG. 2 illustrates that GQDs produced using maltose have peak intensity emissions at about 456 nm when excited at 300 nm, at about 464 nm when excited at 340 nm, at about 470 nm when excited at 360 nm, at about 502 nm when excited at 400 nm, at about 520 nm when excited at 440 nm, and at about 540 nm when excited at 480 nm.

The following examples describe properties of the GQDs produced using glutamic acid and the method steps used in their production.

EXAMPLES

Materials

L-glutamic acid, Ludox SM-30 colloidal silica (30 wt. % suspension in water), hydrogen peroxide, 2,2'-azino-bis(3-ethylbenzothiazoline-6-sulphonic acid) (ABTS), fluorescein isothiocyanate (FITC) isomer I, rhodamine-101 and phosphate buffered saline (PBS) tablet were obtained from Sigma-Aldrich. Deionized water (18.3 MΩ·cm) was produced using a Millipore water purification system.

Synthesis of Glu-GQDs

Glu-GQDs were synthesized by pyrolyzing glutamic acid. Briefly, 2.0 grams (g) of solid glutamic acid was settled into a glass bottle and heated to 210° C. with a heating mantle. After the glutamic acid melted, the colorless liquid turned to a pale yellow and brown after about 45 seconds of boiling. This color change indicated the carbonization of the glutamic acid resulting from pyrolysis and the formation of Glu-GQDs. Following the color change, 10.0 mL of deionized water was added to the Glu-GQD solution followed by stirring for 30 minutes. No surface passivation agents or inorganic additives were needed for the generation of the Glu-GQDs. Once the Glu-GQD solution temperature reached room temperature, the solution was centrifuged (10,000 g, 30 min). The GQD-containing supernatant formed during centrifugation was collected. Though not wishing to be bound by any particular theory, it is believed that residual glutamic acid acted as a surface passivation agent, yielding extremely stable and highly fluorescent Glu-GQDs. The resulting Glu-GQD solution was stored at room temperature for 5 months without precipitation.

Characterization of the Glu-GQDs

A JEOL JEM-2100 high-resolution transmission electron microscope (HRTEM) was used to characterize the Glu-GQDs at an operating voltage of 200 kV. The size distribution of the Glu-GQDs was measured and graphed using an ImageJ Fourier transform infrared (FTIR) spectrometer (Peking). Energy-dispersive X-ray spectroscopy (EDS), performed using a Hitachi SU8010 field scanning electron microscope (SEM) at an operating voltage of 5 kV, was used to analyze the relative content of carbon, nitrogen and oxygen in the glutamic acid and the Glu-GQDs. A Shimadzu UV-250 UV/Vis spectrometer was used for measurements of the UV/Vis absorption spectrum of the Glu-GQDs. The fluorescence spectra, lifetime, and quantum yields were measured using a Jobin-Yvon-Horiba Fluorometer 3 Model FL 3-11 spectrofluorometer. Zeta potential was detected using the Zetasizer (Marlwen, model of Nano-ZS) by adjusting the pH of the Glu-GQDs from 2.0 to 12.0 with PBS.

Figure 8:
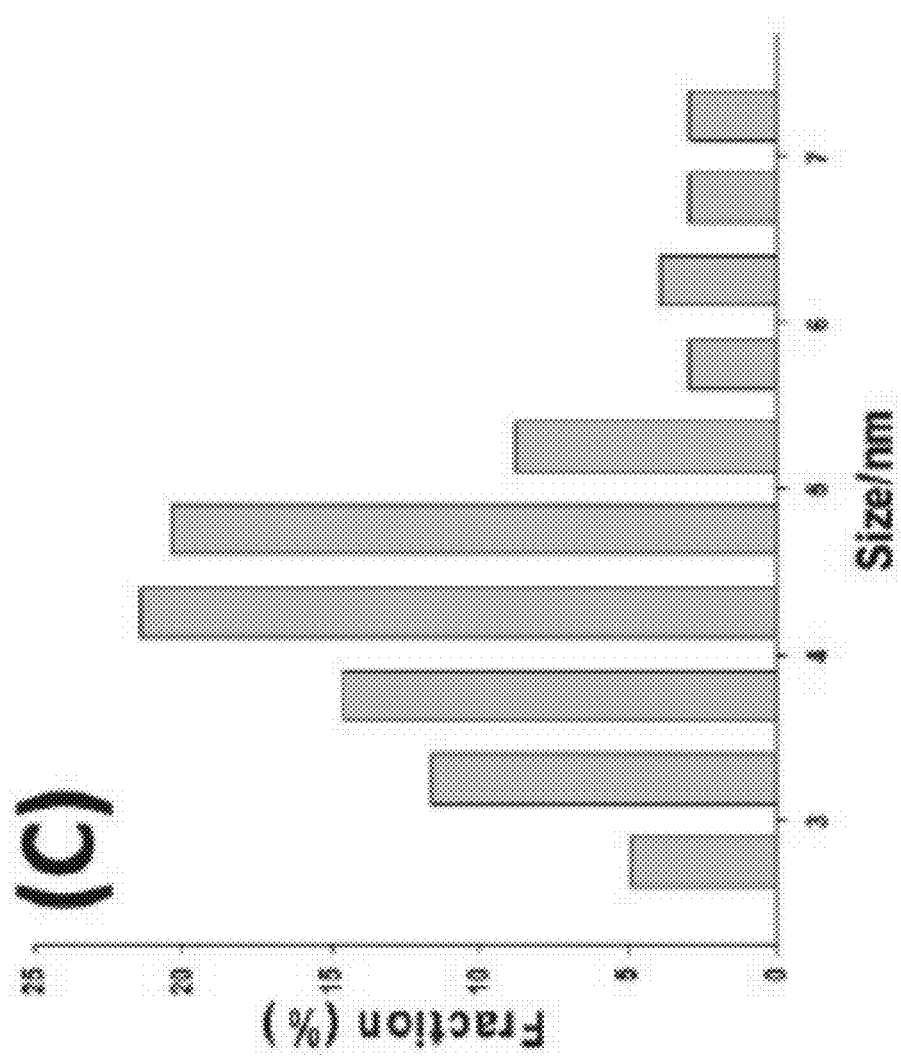
FIG. 8 is a graph showing the size distribution of GQDs formed according to FIG. 1.

The Glu-GQDs' lattice space was measured to be 0.246 nm from a TEM image. The average diameter of the Glu-GQDs was found to be 4.66±1.24 nm according to statistical calculations based on more than 100 individual dots. The size distribution showed uniform dimensions of the prepared Glu-GQDs. FIG. 8 illustrates a graph showing the size distribution of Glu-GQDs prepared as described above.

The element content of Glu-GQDs was analyzed using EDS. As a comparison, the element content of the glutamic acid used to prepare the Glu-GQDs was also analyzed. The EDS results showed that the glutamic acid contained the following element amounts: 48.73% (C), 9.54% (N), and 41.73% (O). Following pyrolysis of the glutamic acid, Glu-GQDs were formed. Compared to the glutamic acid, the carbon content of Glu-GQDs increased from 48.73% to 60.01%. Meanwhile, the oxygen content decreased from 41.73% to 34.60%, and the nitrogen content decreased from 9.54% to 5.39%. This result indicated that the glutamic acid was carbonized as a result of pyrolysis.

Figure 9:
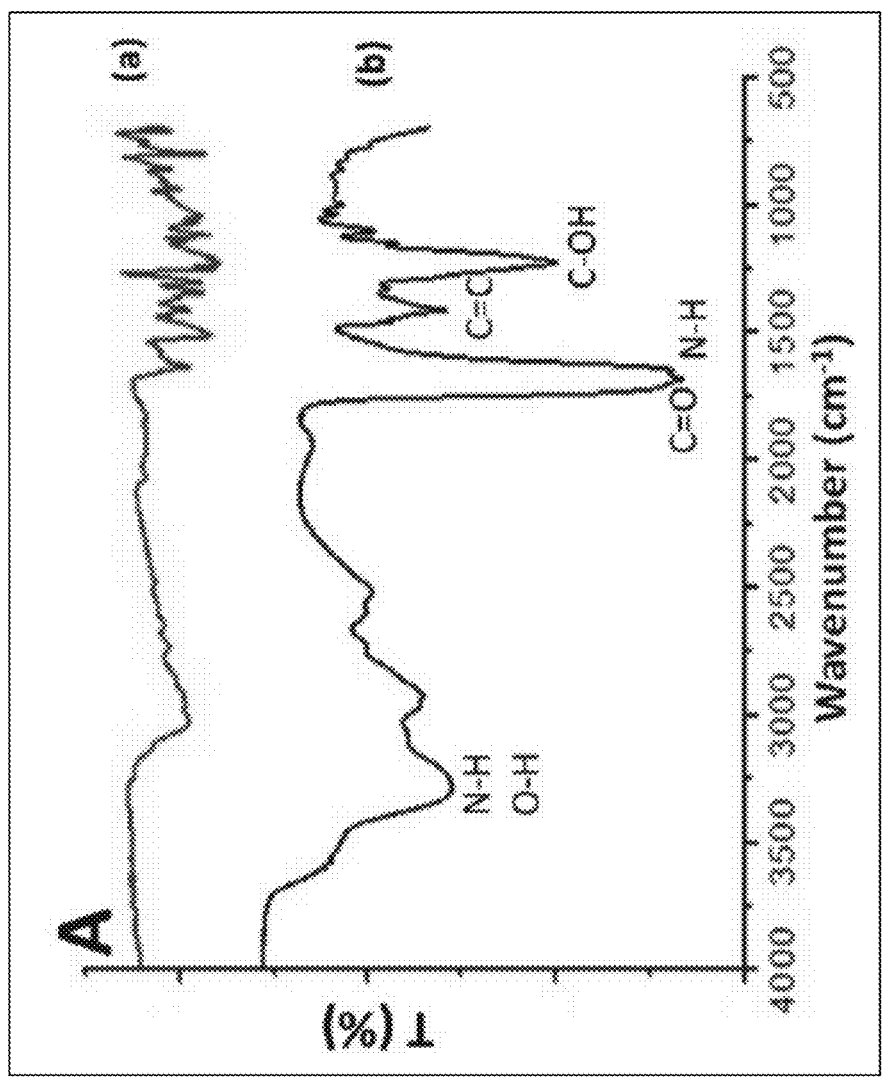
FIG. 9 illustrates FTIR spectra of glutamic acid (a) and GQDs (b) formed according to FIG. 1.

The structural change from glutamic acid to Glu-GQDs was further characterized using FTIR. FIG. 9 illustrates FTIR spectra of glutamic acid (a) and Glu-GQDs (b). The appearance of peaks at 3000 cm$^{-1}$ and 1500 cm$^{-1}$ indicated the stretching of C=C bonds and the formation of Glu-GQDs. The stretching vibrations of O—H, C=O and N—H in spectrum (b) indicated the presence of hydroxyl, carboxyl and amide groups in the Glu-GQDs. The oxygen-containing and nitrogen-containing groups provide high water solubility and stability of the Glu-GQDs in solution.

The zeta potential of Glu-GQDs in different pH values was also investigated. The zeta potential changed from positive 6.81 mV to negative 23.2 mV as pH was increased from 2 to 12. The large zeta potential change is related to the formation of the amino and carboxyl groups in Glu-GQDs. Because of the reaction activity of the amino and carboxyl groups, biomolecules, such as antibodies and aptamers, could be easily conjugated onto Glu-GQDs for further applications.

Fluorescence Properties of Glu-GQDs

Figure 10A:
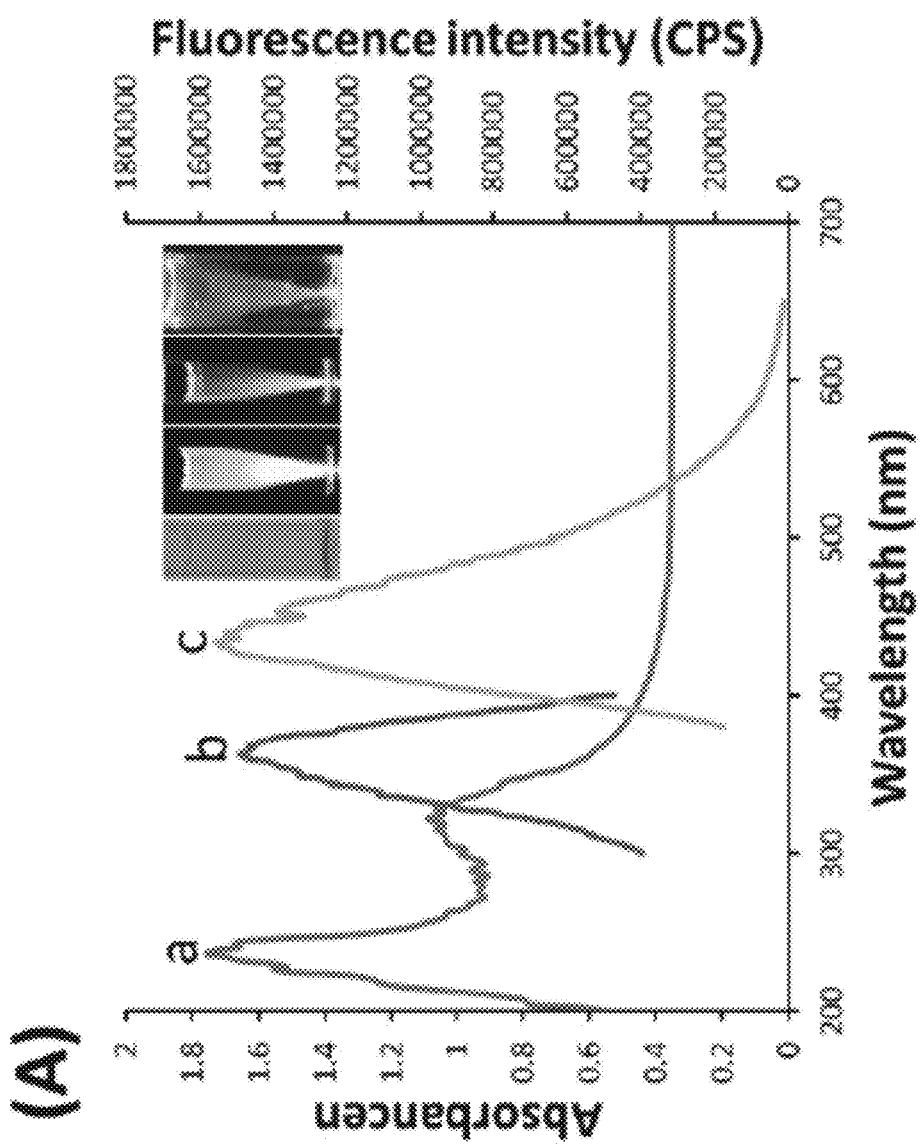
FIG. 10A illustrates UV-vis absorption spectra and photoluminescence (PL) spectra of GQDs formed according to FIG. 1.
Figure 10B:
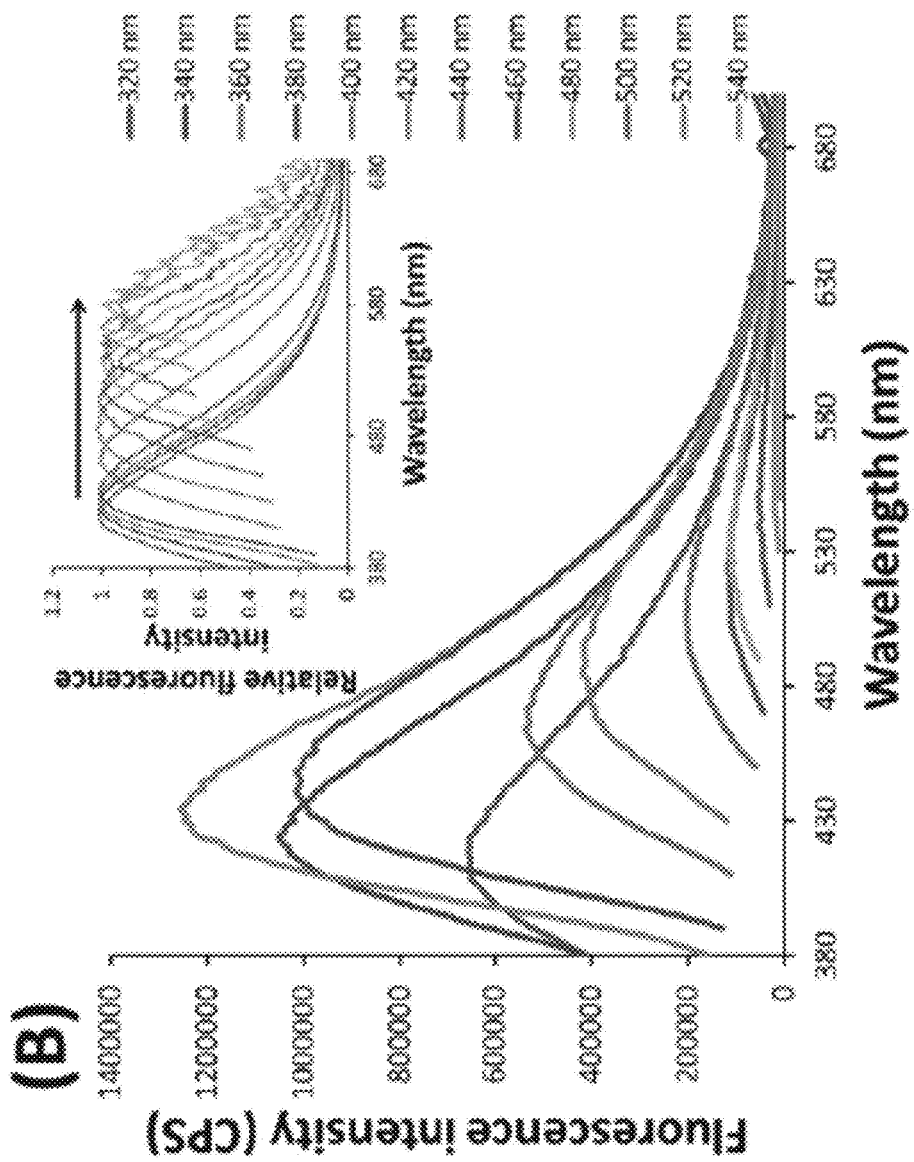
FIG. 10B illustrates fluorescence emission spectra of GQDs formed according to FIG. 1.

A key feature of Glu-GQDs prepared according to the present disclosure is displayed in their fluorescence properties. FIG. 10A illustrates UV-vis absorption spectra and photoluminescence (PL) spectra of Glu-GQDs. The Glu-GQDs showed two obvious absorption peaks at 238 nm and 335 nm, respectively (curve a). The peak around 238 nm is attributed to π-π* transitions of C=C bonds. The apparent peak at 335 nm indicates the uniform size of the sp² clusters in the Glu-GQDs even though these sp² clusters were doped in the sp³ matrix. When Glu-GQDs were excited at 360 nm (curve b), the Glu-GQDs showed a strong fluorescence peak at 440 nm (curve c). This fluorescence is strong enough to be observed by the naked eye. This feature indicated the high quantum yield of Glu-GQDs and their promising applications for fluorescence imaging. In addition, fluorescence emission spectra showed an excitation-dependent behavior. The emission peak of the Glu-GQDs shifted from 415 nm (violet) to 580 nm (red) when the excitation wavelength was changed from 320 nm to 540 nm. FIG. 10B illustrates fluorescence emission spectra of Glu-GQDs.

The fluorescence properties of Glu-GQDs were also investigated using a fluorescence microscope. With the irradiation of violet (330-385 nm), blue (460-500 nm) and green (535-585 nm) light, the Glu-GQDs emitted strong blue, green and red fluorescence, respectively. The Glu-GQD precursor (glutamic acid) showed no absorption in the violet region and no fluorescence in the range of violet to visible. Thus, all of these fluorescence properties are related to the formation of Glu-GQDs.

Detection of Quantum Yields

The fluorescence quantum yield and lifetime of Glu-GQDs was measured. Quantum yield was calculated according to the equation:

$$\Phi_X = \Phi_{ST}\left(\frac{Grad_X}{Grad_{ST}}\right)\left(\frac{\eta_X^2}{\eta_{ST}^2}\right)$$

where the subscripts ST and X denote standard and test respectively, and where Φ, Grad and η are the quantum yield, gradient from the plot of integrated fluorescence intensity vs. absorbance, and refractive index of the solvent, respectively. Rhodamine 101 in ethanol (QY=1.0) was chosen as a reference. The refractive index for the standard and test are 1.36 and 1.33 respectively. Rhodamine 101 was excited at 560 nm and with emission of 565-700 nm. The Glu-GQDs were excited at 360 nm and with emission of 380-650 nm. Using Rhodamine 101 as a reference dye, the quantum yield of Glu-GQDs was found to be 63.8% under excitation at 360 nm. This relatively high quantum yield may have benefited from the protection of residual glutamic acid as a surface passivation agent.

Detection of Lifetime

The fluorescence lifetime of Glu-GQDs was analyzed using the time-correlated single photon counting (TCSPC) method at different emission wavelengths with 370 nm LED excitation. A sample of Ludox SM-30 colloidal silica was used as the reference. The fluorescence emissions tested showed well-fitting triple-exponential function. The observed lifetimes of Glu-GQDs at 445 nm, 505 nm and 650 nm are summarized in Table 1. The average fluorescence lifetime was in the range of 0.31 nanoseconds to 0.50 nanoseconds. The observed lifetime of Glu-GQDs demonstrate promise for optoelectronic and biological applications.

TABLE 1

| Excit. (nm) | Emit. (nm) | $\tau_1$ (ns) | $\tau_2$ (ns) | $\tau_3$ (ns) | Av. τ (ns) | Chi |
|---|---|---|---|---|---|---|
| 370 | 445 | 0.81 | 3.64 | 11.55 | 0.50 | 1.14 |
| 370 | 505 | 3.78 | 0.80 | 12.04 | 0.50 | 1.27 |
| 370 | 650 | 2.35 | 6.77 | 0.47 | 0.31 | 1.13 |

Figure 11:
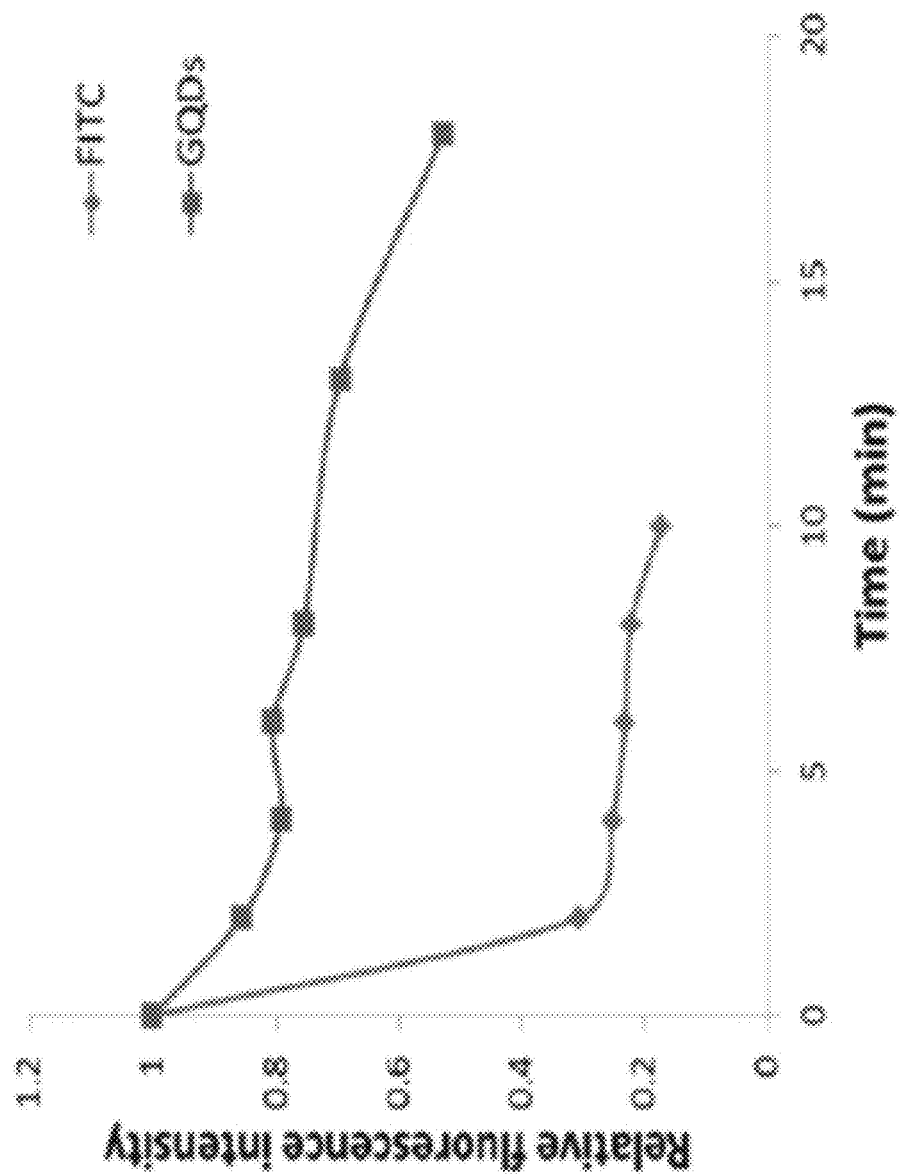
FIG. 11 illustrates the photostability of FITC and GQDs formed according to FIG. 1.

Compared to traditional organic dyes, such as Fluorescein isothiocyanate (FITC), the Glu-GQDs can not only emit fluorescence at different wavelengths, but also show much higher photostability. The fluorescence of FITC was bleached by 70% under a confocal laser in about 2 minutes. However, the fluorescence of Glu-GQDs still showed strong fluorescence intensity, only 47% bleached, even after 18 min of the same irradiation. FIG. 11 illustrates the relative photostability of FITC and Glu-GQDs. This higher photostability provides Glu-QGDs with high potential for in vitro and in vivo fluorescence imaging, discussed in greater detail below.

Figure 12:
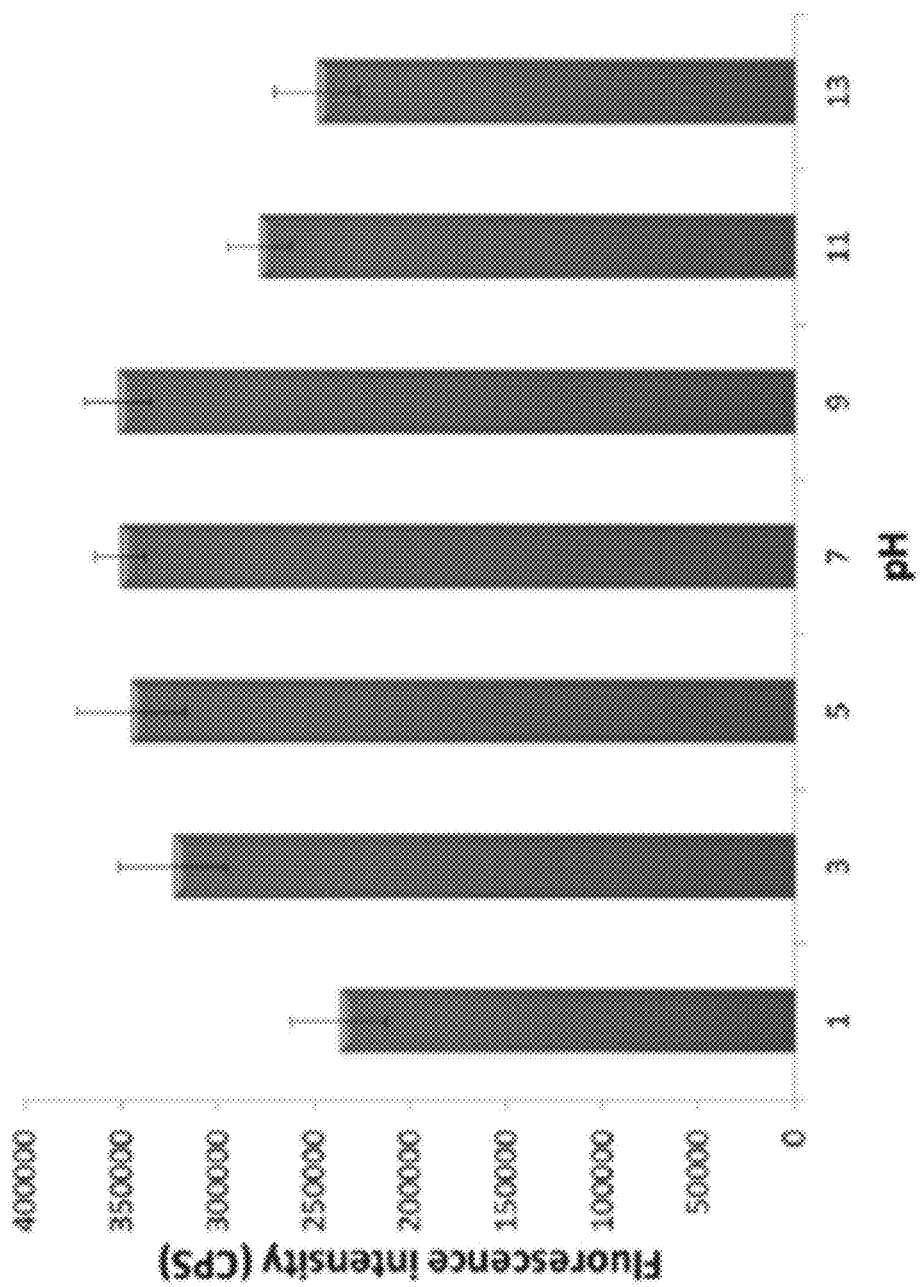
FIG. 12 illustrates the fluorescence intensity of GQDs formed according to FIG. 1 at different pH values.

The stability of Glu-GQDs at different pH values was also investigated. FIG. 12 illustrates the fluorescence intensity of Glu-GQDs at different pH values. Results showed that Glu-GQDs had the highest fluorescence intensity at pH 7.0. In the range of pH 5.0-9.0, changes in the fluorescence intensity were less than 1.4%. This range covers the majority of pH values in living systems. When pH was below 5.0 or higher than 9.0, the fluorescence intensity of the Glu-GQDs was reduced by 32.3%. The significant stability of Glu-GQDs over the large range of pH may come from the surface amino group and carboxyl group, which could resist pH effects on the fluorescence intensity of Glu-GQDs.

Figure 13A:
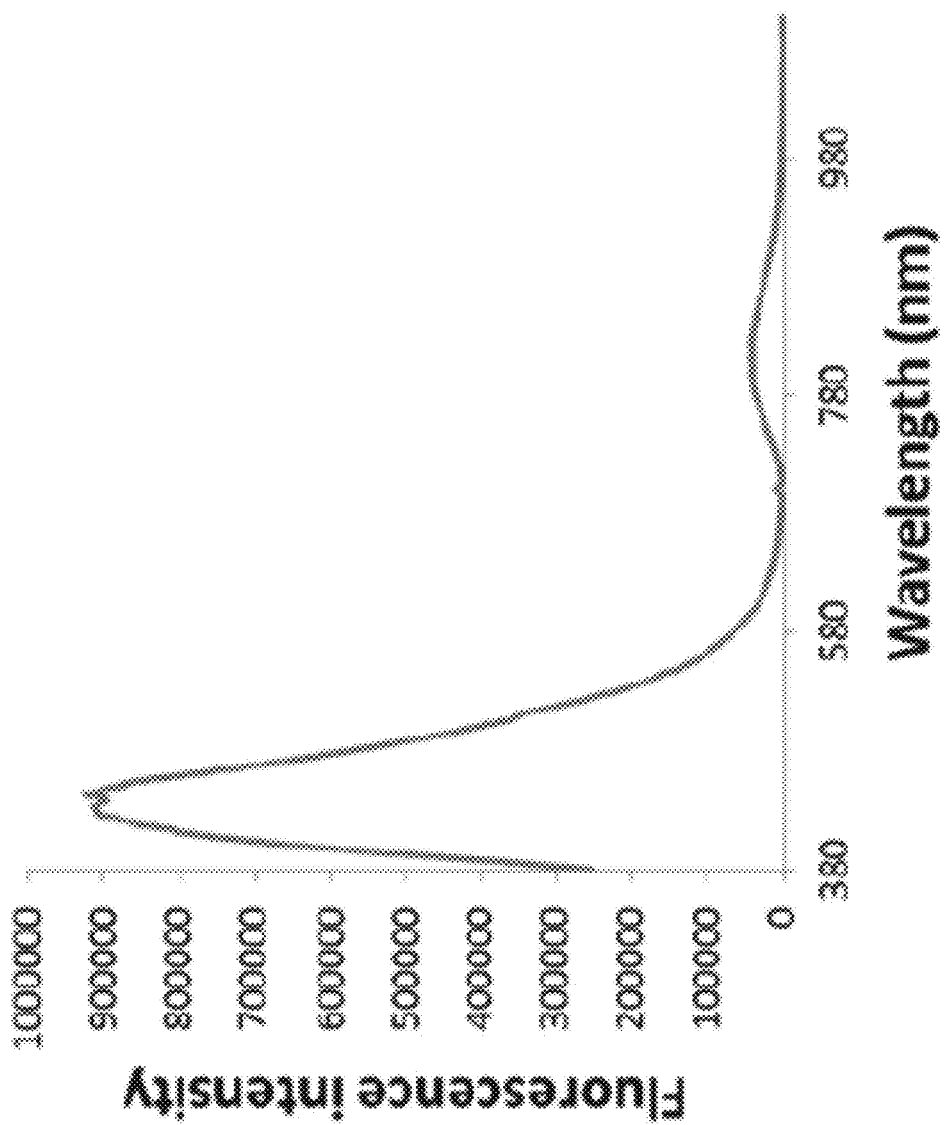
FIGS. 13A, 13B and 13C are fluorescence emission spectra of GQDs formed according to FIG. 1.
Figure 13B:
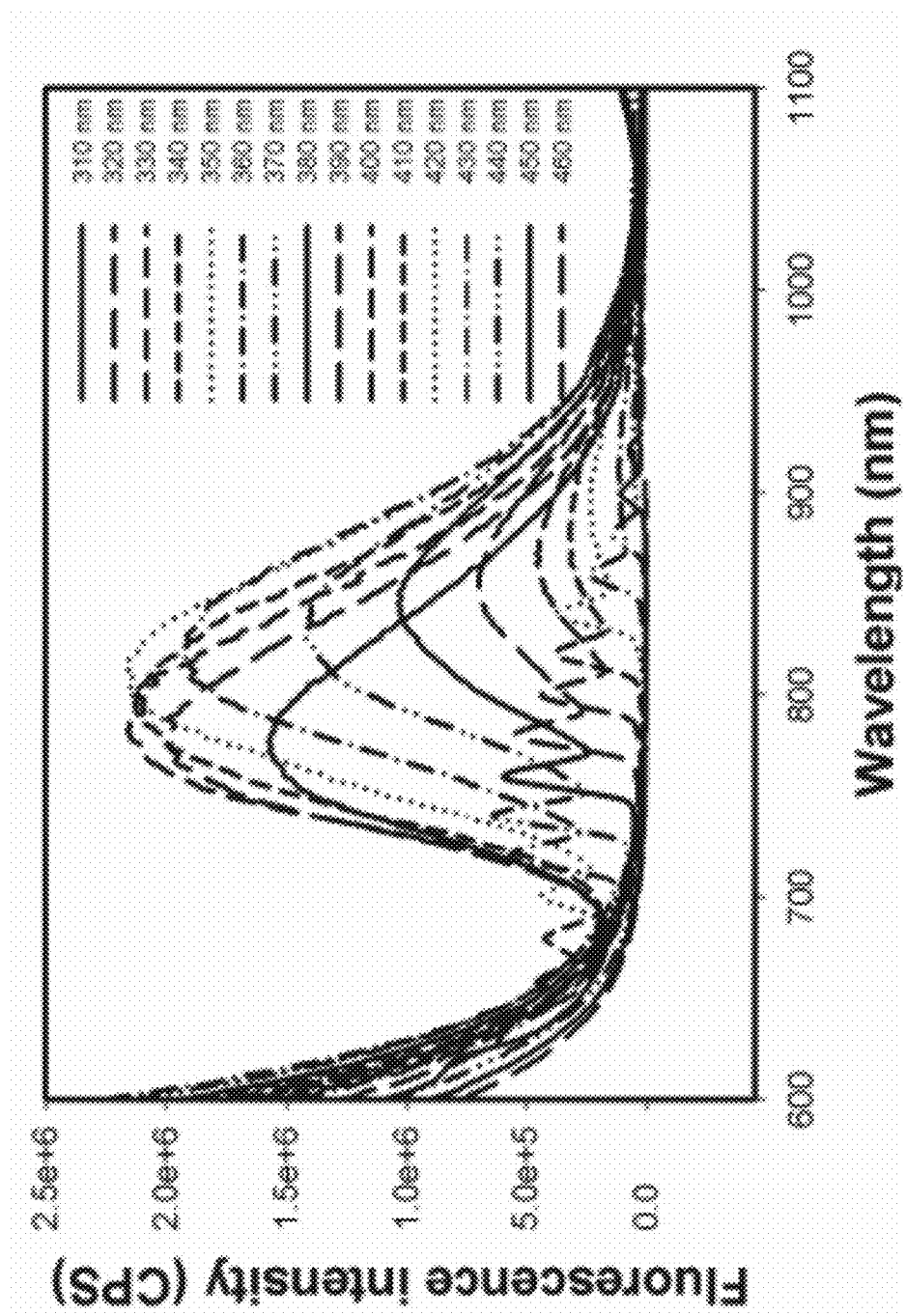
Figure 13C:
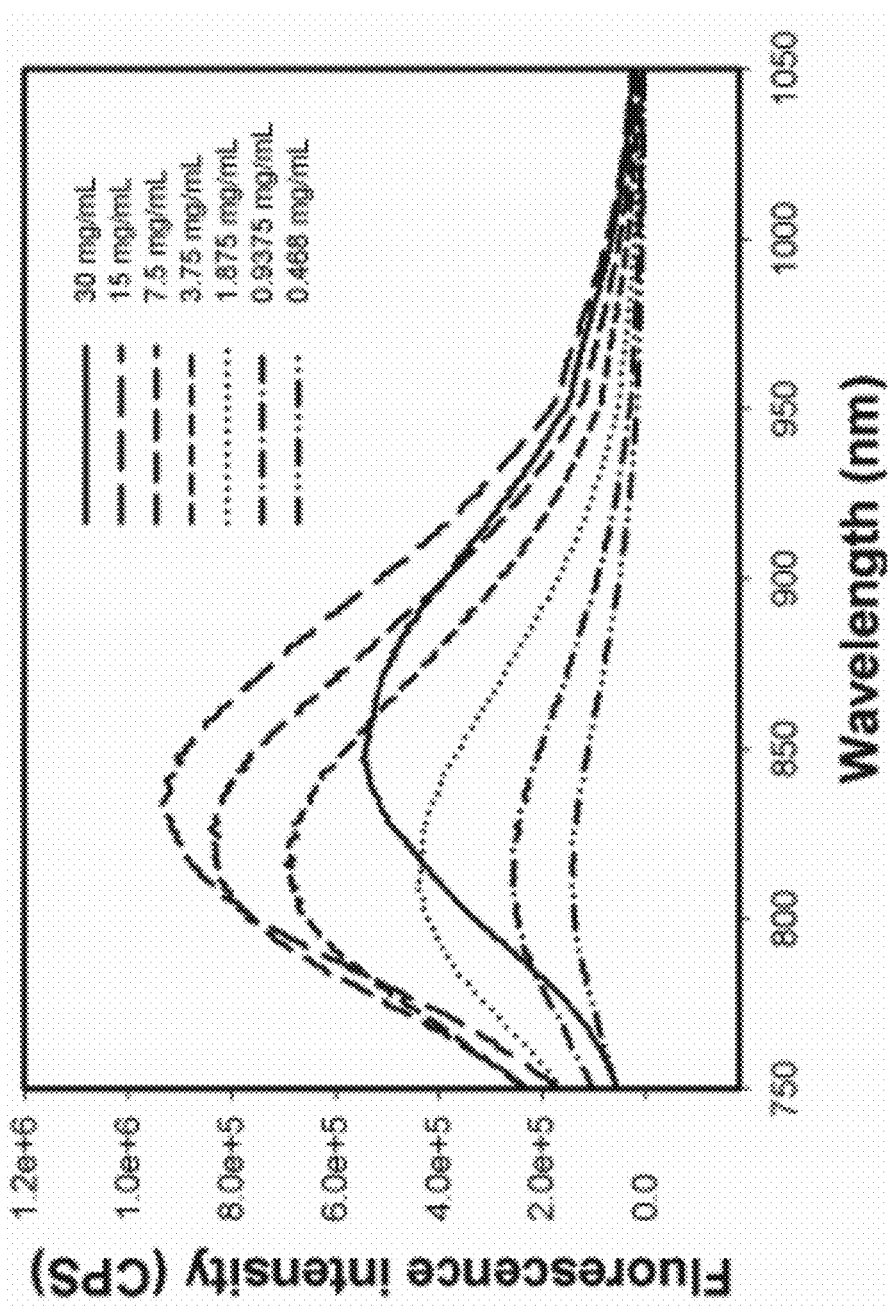

Besides the fluorescence emission in blue, green and red regions, the Glu-GQDs emitted a relatively lower near infrared (NIR) fluorescence around 815 nm with irradiation at 360 nm. The intensity ratio of 815 nm to 440 nm was 0.2 according to the fluorescence spectra (FIG. 13A). The NIR peak was significantly higher than the 2λ diffraction peak shown in FIG. 13B. Similar to the fluorescence property in the visible region, the peak in the NIR region showed red shift when the excitation wavelength was increased. The fluorescence intensity of the Glu-GQDs in the NIR region was proportional to the concentration of the Glu-GQDs in the range of 0.468-15.0 mg/mL (FIG. 13C). This relationship indicates that the NIR fluorescence must be attributed to the Glu-GQDs even though the mechanism is not clear yet. With this NIR fluorescence, whose Stock shift was as large as 450 nm, these Glu-GQDs can be very useful for fluorescence bioimaging and biosensing. In the NIR region, biological samples typically have low background fluorescence signals, providing high signal to noise ratio for the Glu-GQDs. Additionally, NIR radiation can penetrate into sample matrices deeply due to low light scattering. Thus, Glu-GQDs are promising labeling reagents for sensitive determination and imaging of biological targets. The result showed a value similar to that of the visible fluorescence described above.

In Vitro Fluorescence Imaging of Cells

The fluorescence imaging of a cell treated with Glu-GQDs was detected with laser confocal microscopy under different excitation wavelengths (Zeiss LSM-510 Meta Confocal Microscope). Briefly, murine alveolar macrophage cells (MH-S) were cultured overnight at 37° C. on plates in RPMI 1640 medium containing 10% fetal bovine serum in a 5% $CO_2$ environment. The cultured cells were washed twice with PBS (pH 7.4). Afterwards, a 2-mL aliquot of 10 mg/mL Glu-GQDs in PBS was added to the cell culture medium followed by a 1-hour culture at 37° C. in a 5% $CO_2$ environment. The cultured cells were washed twice using PBS and imaged using the Zeiss LSM-510 Meta confocal microscope. The MH-S cells incubated with Glu-GQDs in PBS showed strong green (LP 475) and red (LP 530) colors upon excitation at 458 nm and 514 nm, respectively. However, no similar fluorescence was observed from the control group that was not incubated with the Glu-GQDs. These results demonstrate that Glu-GQDs can emit strong fluorescence in the green to red range under different excitation wavelengths for in vitro fluorescence imaging.

In Vivo Fluorescence Imaging of Mice

The in vivo fluorescence imaging of mice treated with Glu-GQDs was carried out using an IVIS imaging system (IVIS Lumina XR, Caliper). Male athymic BALB/c-nu mice with weights of 20-25 grams were obtained from Charles River (Wilmington, Mass.) and maintained in the University of North Dakota Animal Center. All animal operations were in accord with approved institutional animal use and care regulations. The feasibility of the Glu-GQDs for in vivo fluorescence imaging was investigated by subcutaneous and intramuscular injection. The mice were anesthetized and injected with a 100-μL aliquot of a 25 mg/mL GQD PBS solution (pH 7.4) subcutaneously on the back and a 100-μL aliquot of the 25 mg/mL GQD PBS solution intramuscularly in the right back leg. The fluorescence images of the mice under different excitation and emission filters were captured.

Various excitations from blue to red centered at 430 nm, 465 nm, 500 nm, 535 nm and 605 nm were used for in vivo fluorescence imaging. The following emission bandpass filters were used: GFP: 515-575 nm; DsRed: 575-650 nm; and Cy5.5: 695-770 nm. As the excitation wavelength increased, fluorescence intensity decreased. Moreover, the detectable fluorescence region had extended with the longer excitation and emission wavelengths from the intramuscularly injection spot on the right back leg. This result demonstrated that the longer wavelengths had better penetration ability than the shorter wavelengths for in vivo fluorescence imaging. Considering the decreased fluorescence intensity at the longer excitation wavelengths, the optimal excitation and emission bandpass to obtain the highest signal-to-background ratio should be investigated for further imaging applications. The in vivo fluorescence imaging in mice under subcutaneous and intramuscular injection indicated that Glu-GQDs can be used as a fluorescent labeling agent for bioimaging in both the visible and NIR regions.

Detection of $H_2O_2$ Based on Glu-GQD's Catalytic Activity

In addition to their optical properties, the catalytic abilities of Glu-GQDs were also investigated. It was reported that materials containing aromatic $sp^2$ carbon clusters had an intrinsic peroxidase-like catalytic activity which produced a blue color reaction in the presence of $H_2O_2$ and peroxidase substrate 3,3,5,5-tetramethylbenzidine (TMB). For example, both carbon nanotubes and graphene sheets were used for the label-free detection of glucose and single-nucleotide polymorphism through their intrinsic peroxidase-like catalytic activity. Inspired by this work, Glu-GQDs formed as described above were tested to determine whether they could be used for label-free colorimetric sensing as a catalyst.

Figure 14:
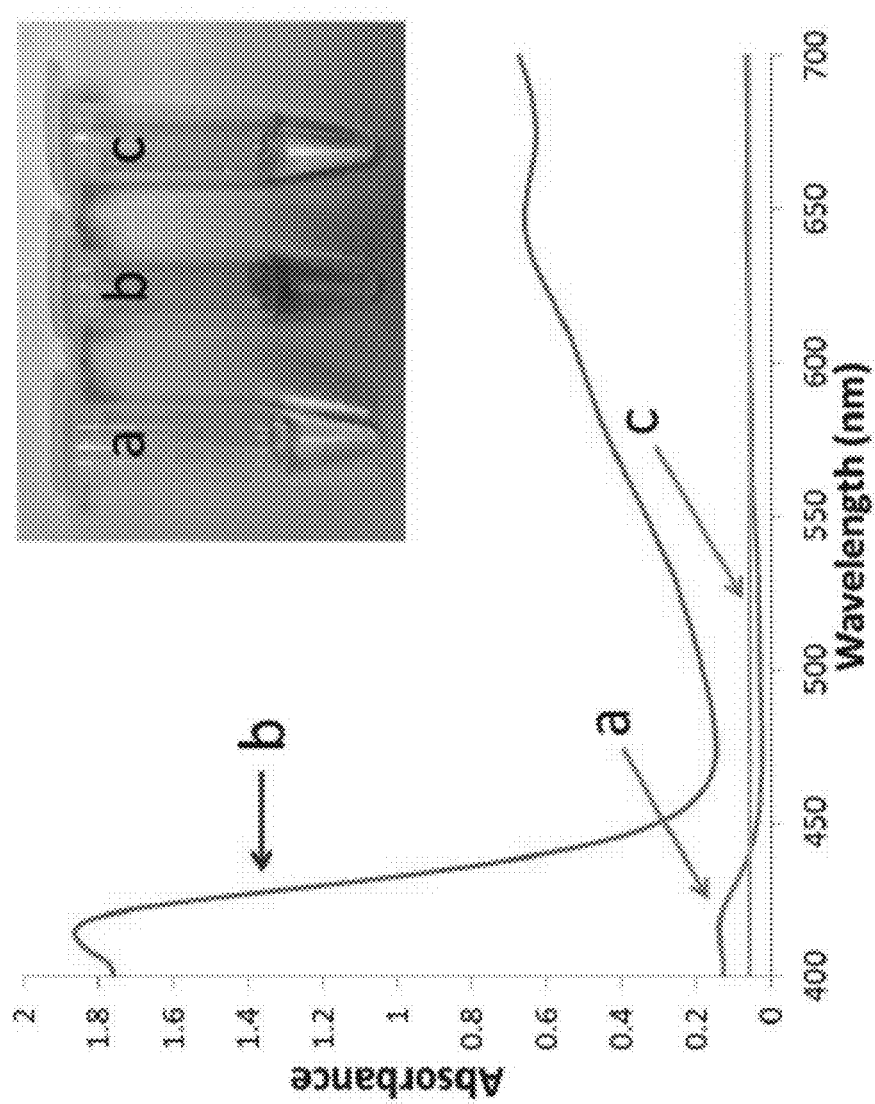
FIG. 14 is a UV-vis absorption spectra showing the ability of GQDs formed according to FIG. 1 to detect the presence of $H_2O_2$.

A solution containing 5.4 mg/mL Glu-GQDs was dissolved in 110 μL of 10 mM Tris-HCl buffer (pH 5.0), followed by the addition of 7.2 mM 2,2'-azino-bis(3-ethylbenzothiazoline-6-sulphonic acid) (ABTS). Hydrogen peroxide ($H_2O_2$) was added to the Glu-GQD/ABTS solution. The absorption spectra of $H_2O_2$ (curve a), the Glu-GQD/ABTS solution with $H_2O_2$ (curve b), and the Glu-GQD/ABTS solution without $H_2O_2$ (curve c) were recorded after 2 minutes of reaction time and are illustrated in FIG. 14.

With the addition of $H_2O_2$, the Glu-GQDs catalyzed the reduction of hydrogen peroxide, indicated by the color change of the solution to green in the presence of the peroxidase substrate ABTS. The absorbance change of ABTS at 416 nm can be used for monitoring the reaction rate and the peroxidase-like catalytic activity of Glu-GQDs. Compared to the control groups including the solution without Glu-GQDs or $H_2O_2$, the signal-to-background ratio was higher than 9. Thus, the peroxidase-like catalytic activity of Glu-GQDs can be used for the detection of $H_2O_2$.

Figure 15B:
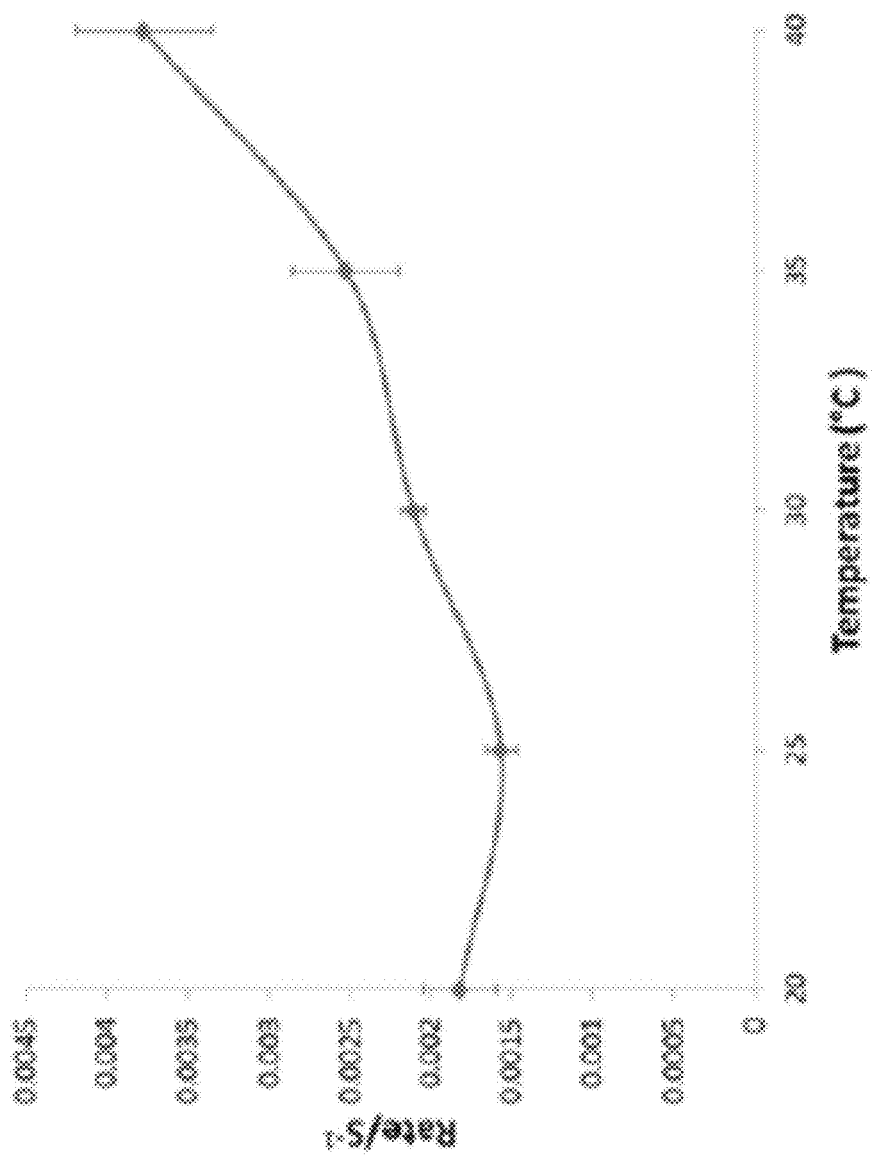
Figure 15C:
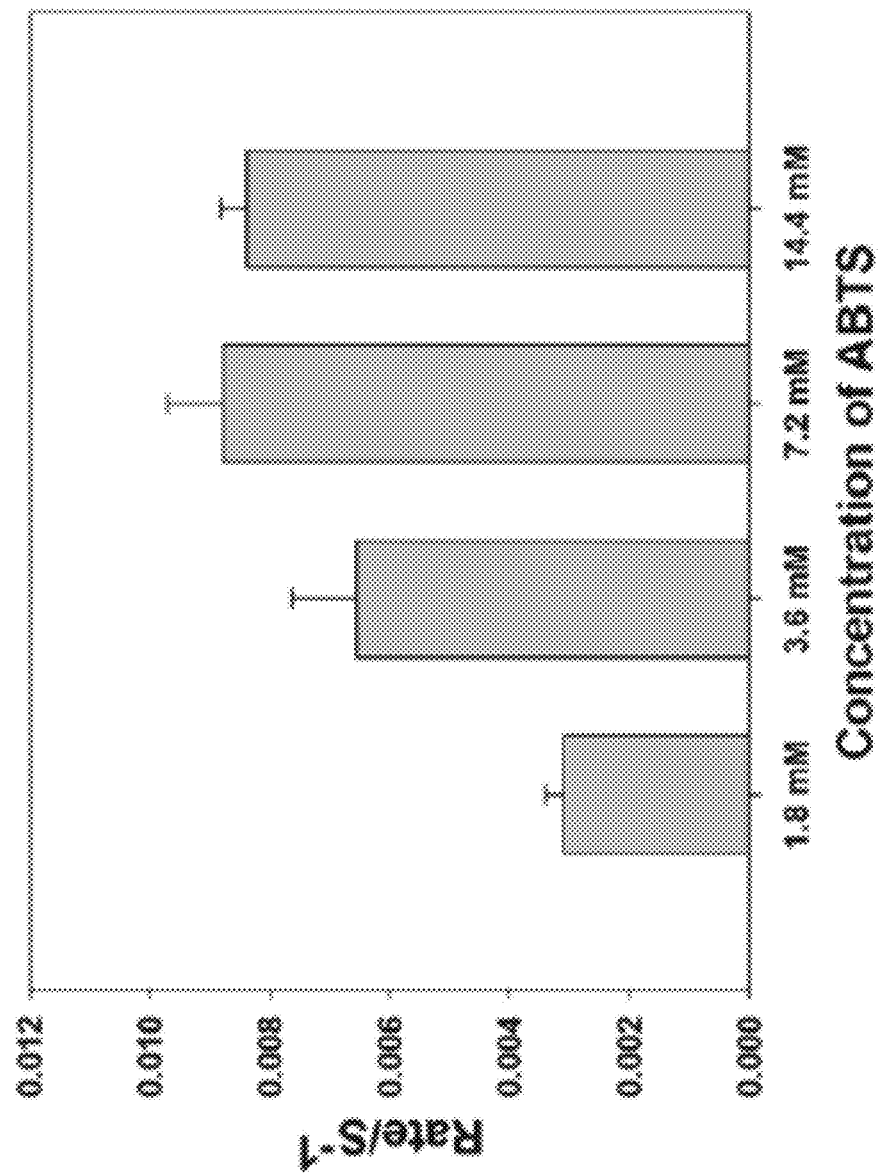
Figure 15D:
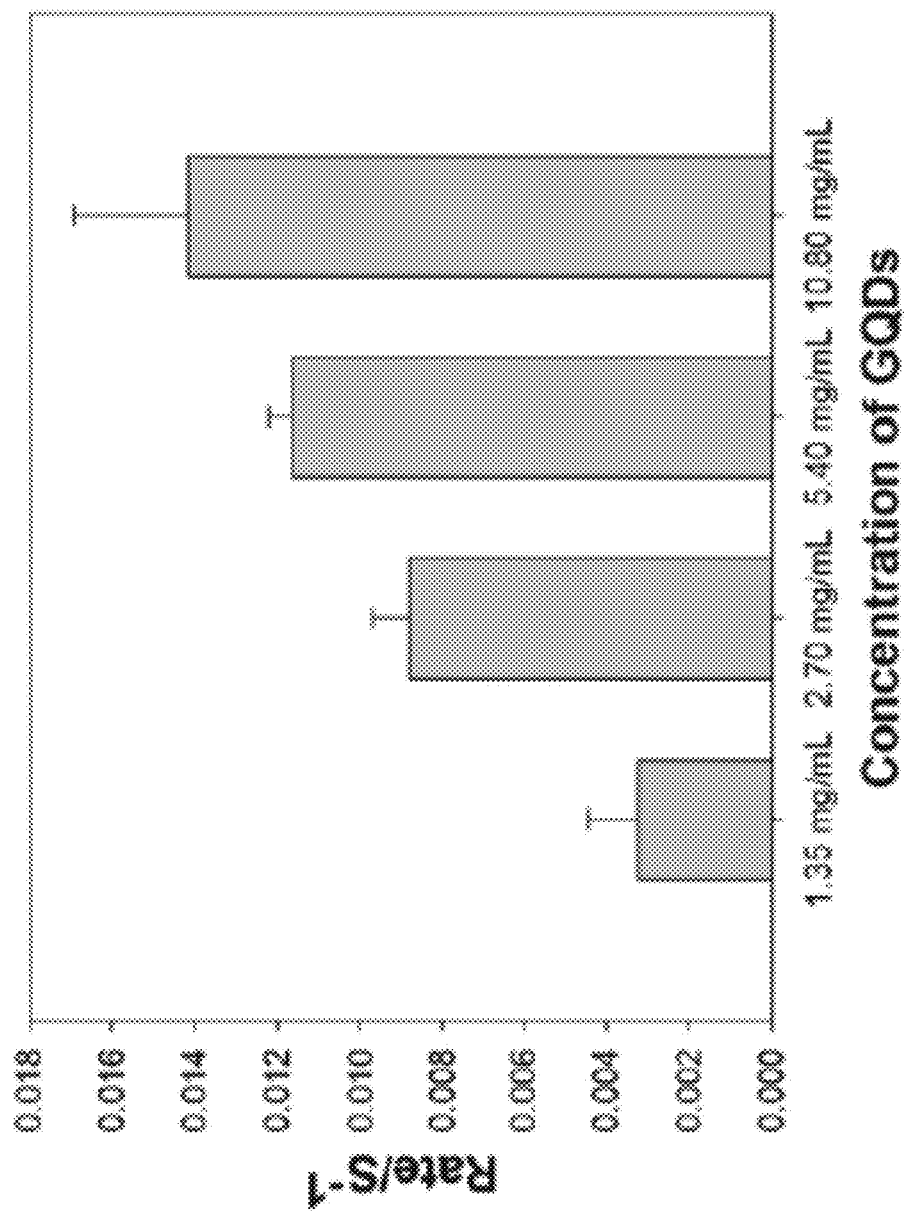

The detection conditions for catalyzing the $H_2O_2$ reaction using the Glu-GQDs were optimized. The optimized conditions included pH, reaction temperature, and the concentrations of ABTS and the Glu-GQDs. The pH value was found to be a critical factor for the detection of $H_2O_2$. It was previously reported that the optimal pH for a carbon nanoparticle catalyzed $H_2O_2$ reaction was 4.0. Our results showed that, at a low pH range (3.0-5.0), the reaction rate was very stable (FIG. 15A). However, the reaction rate decreased above pH 5.0. Therefore, pH 5.0 was chosen as the optimal pH. The reaction temperature was also found to affect the catalytic reaction rate. As shown in FIG. 15B, a higher temperature would increase the reaction rate. Normal human body temperature (37° C.) was selected as the standard condition for analyzing $H_2O_2$. The use of ABTS as a substrate was found to affect the sensitivity of the colorimetric detection of $H_2O_2$. As shown in FIG. 15C, the reaction rate increased as the concentration of ABTS increased until it reached a concentration of 7.2 mM. Therefore, 7.2 mM of ABTS was chosen as the optimal concentration. The concentration of the Glu-GQDs was found to be proportional to the reaction rate (FIG. 15D). However, a high concentration of Glu-GQDs could affect the absorption of the ABTS. Therefore, a concentration of 5.40 mg/mL Glu-GQDs was chosen as the optimal concentration for detection.

Figure 16A:
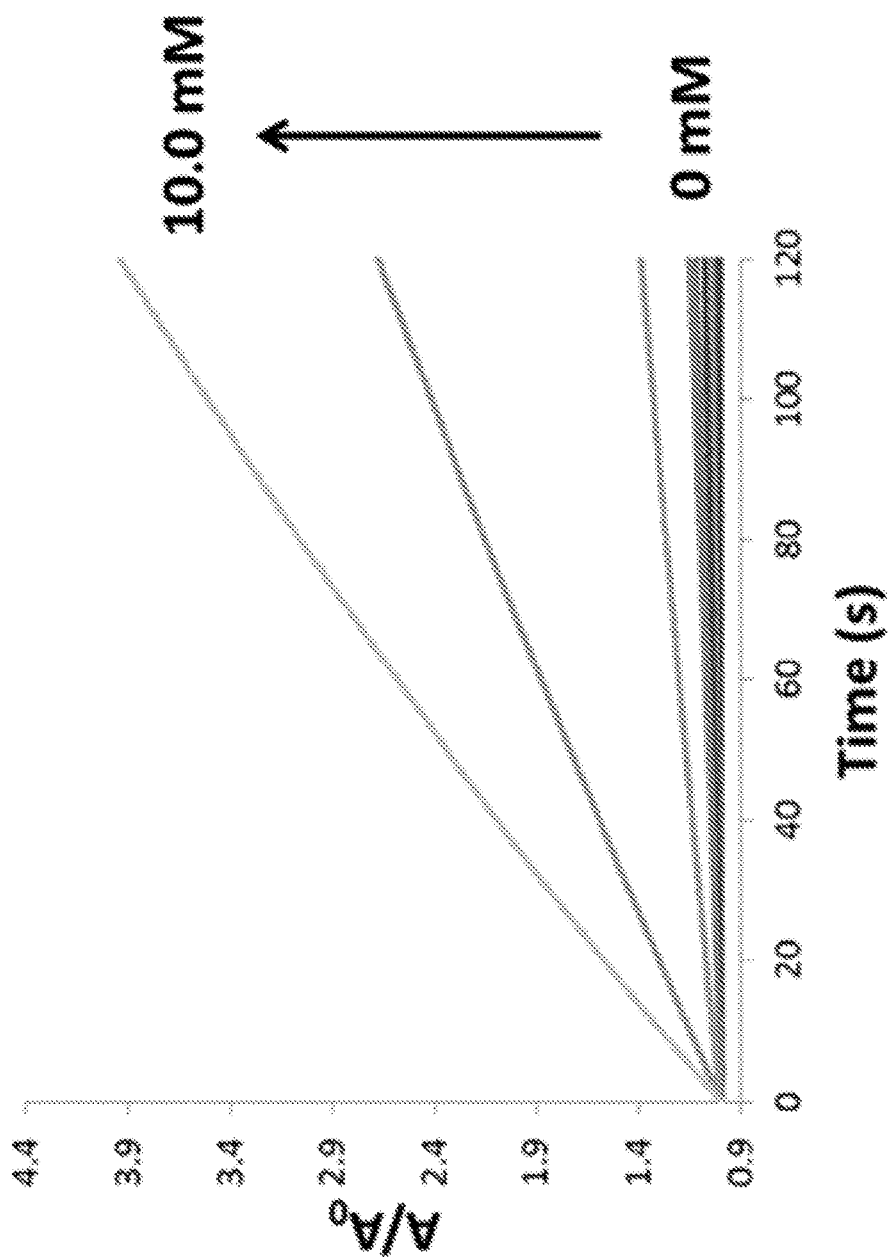
FIG. 16A is a graph illustrating the change in absorbance relative to the $H_2O_2$ concentration.
Figure 16B:
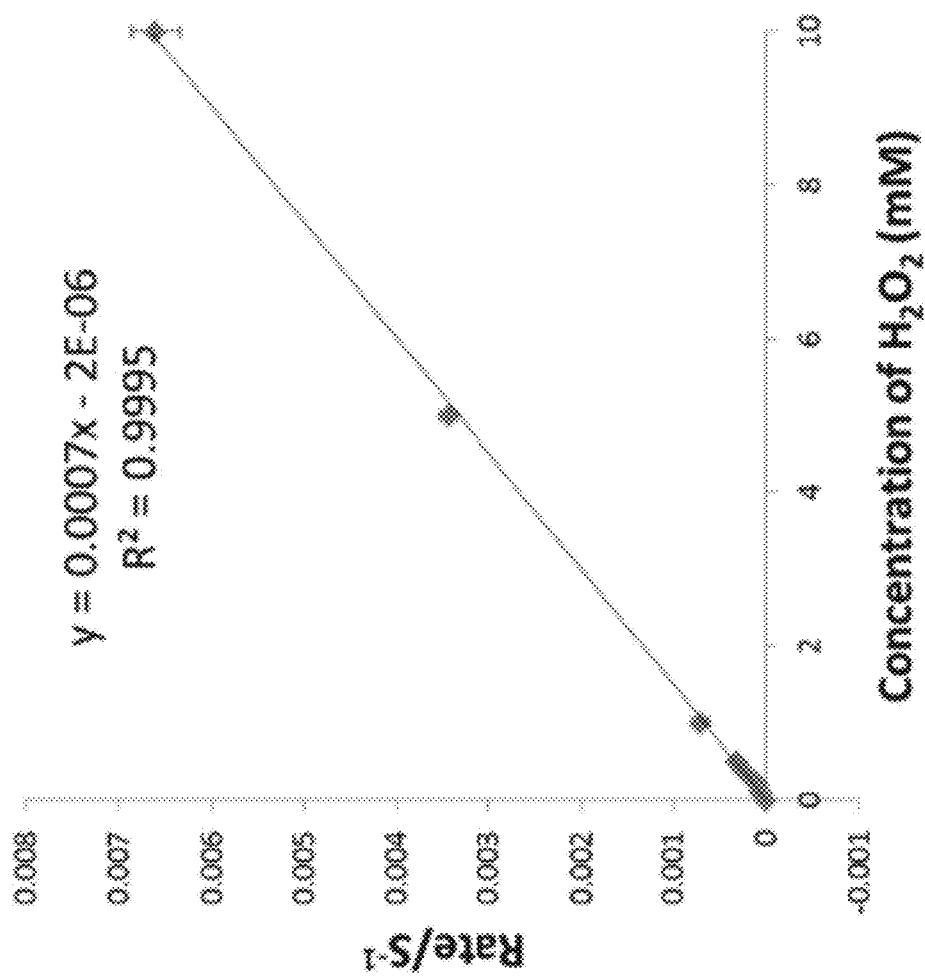
FIG. 16B is a graph illustrating the rate of reaction relative to the $H_2O_2$ concentration.

Under the above optimized conditions, the detection of $H_2O_2$ was carried out using this Glu-GQD-based label-free colorimetric system. As shown in FIG. 16A, with the increase of the concentration of $H_2O_2$, the absorbance increased in a concentration-dependent manner. This assay provides rapid detection (2 min) of $H_2O_2$ with a linear range of $H_2O_2$ from 0.1 mM to 10 mM (FIG. 16B). The limit of detection was found to be 20 μM according to the calibration curve at a signal-to-background ratio of 3.

Glu-GQDs formed according to the present disclosure offer excellent fluorescence properties and peroxidase-like activity. These Glu-GQDs, developed using a direct and simple pyrolysis of glutamic acid, not only show a stable, strong excitation-dependent photoluminescence with high quantum yield (63.8%) in the blue to red range, but also provide an excitation-dependent NIR fluorescence emission around 815 nm. Though the mechanism of this NIR fluorescence emission is not well understood, the application potential of the NIR fluorescence is significant. By using strong visible irradiation, Glu-GQDs show the potential to be used for both in vitro and in vivo fluorescence imaging. Furthermore, Glu-GQDs possess a peroxidase-like activity that can catalyze the reduction of $H_2O_2$. With this unique activity, $H_2O_2$ can be detected using a label-free colorimetric method.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims.

The invention claimed is:

1. A method for forming graphene quantum dots comprising:
adding an amino acid starting material to a vessel; and
heating the amino acid starting material in the absence of a solvent for a time no longer than ten minutes to pyrolyze the amino acid starting material and form graphene quantum dots.

2. The method of claim 1, wherein the amino acid starting material is selected from the group consisting of glutamic acid, aspartic acid, tyrosine, serine, threonine, asparagine, glutamine, alanine, glycine, leucine, lysine and combinations thereof.

3. The method of claim 1, further comprising:
adding a solvent to the graphene quantum dots to form a colloidal solution containing graphene quantum dots;
mixing the solution for between 15 minutes and 60 minutes; and
centrifuging the solution after mixing to obtain a supernatant comprising a concentrated graphene quantum dot product.

4. The method of claim 3, wherein the solvent is selected from the group consisting of water, alcohols and combinations thereof.

5. The method of claim 1, wherein the amino acid starting material is heated for a time less than five minutes.

6. The method of claim 5, wherein the amino acid starting material is heated for a time less than 60 seconds.

7. The method of claim 1, wherein the amino acid starting material is heated until the amino acid starting material changes from a substantially colorless solution to a solution having a yellow color.

8. The method of claim 1, wherein the amino acid starting material comprises glutamic acid, and wherein the organic starting material is heated to a temperature of about 210° C.

9. The method of claim 1, wherein the graphene quantum dots have an average diameter between 1 nanometer and 7 nanometers.

10. The method of claim 1, wherein the graphene quantum dots comprise:
between 55% and 65% carbon atoms;
between 30% and 40% oxygen atoms; and
between 3.5% and 7.5% nitrogen atoms.

11. The method of claim 1, wherein the graphene quantum dots comprise nitrogen atoms at a level between 6.0% and 11.0% of a level of carbon atoms present in the graphene quantum dots.

12. The method of claim 1, wherein the graphene quantum dots are capable of catalyzing reduction of hydrogen peroxide.

* * * * *